(12) United States Patent
Rabovsky et al.

(10) Patent No.: US 8,273,393 B2
(45) Date of Patent: Sep. 25, 2012

(54) MINERAL AMINO ACID POLYSACCHARIDE COMPLEX

(75) Inventors: Alexander B. Rabovsky, Idaho Falls, ID (US); Jeremy Ivie, Ammon, ID (US)

(73) Assignee: Melaleuca, Inc., Idaho Falls, ID (US)

( * ) Notice: Subject to any disclaimer, the term of this patent is extended or adjusted under 35 U.S.C. 154(b) by 386 days.

(21) Appl. No.: 12/499,929

(22) Filed: Jul. 9, 2009

(65) Prior Publication Data

US 2010/0009901 A1  Jan. 14, 2010

Related U.S. Application Data

(60) Provisional application No. 61/079,176, filed on Jul. 9, 2008.

(51) Int. Cl.
*A23L 1/29* (2006.01)
*A23L 1/304* (2006.01)
*A23L 1/305* (2006.01)
*C08B 37/00* (2006.01)

(52) U.S. Cl. .......... 426/72; 426/74; 426/271; 536/123.1

(58) Field of Classification Search .................... 426/72, 426/74, 271; 536/123.1
See application file for complete search history.

(56) References Cited

U.S. PATENT DOCUMENTS

| | | | |
|---|---|---|---|
| 4,863,898 A * | 9/1989 | Ashmead et al. | ............... 514/5.4 |
| 5,292,538 A * | 3/1994 | Paul et al. | ........................ 426/74 |
| 5,773,227 A | 6/1998 | Kuhn et al. | |
| 6,207,204 B1 | 3/2001 | Christiansen et al. | |
| 7,153,503 B1 | 12/2006 | Henderson | |
| 2005/0053696 A1 | 3/2005 | Akashe et al. | |
| 2005/0064070 A1* | 3/2005 | Liebrecht | ........................ 426/72 |
| 2005/0239750 A1 | 10/2005 | Motyka et al. | |
| 2005/0239763 A1 | 10/2005 | Motyka et al. | |
| 2005/0255147 A1 | 11/2005 | Geach | |
| 2006/0069062 A1 | 3/2006 | Shiomi et al. | |
| 2007/0092461 A1 | 4/2007 | Gupta | |
| 2007/0099886 A1 | 5/2007 | Gupta | |
| 2007/0286916 A1 | 12/2007 | Bengmark | |

FOREIGN PATENT DOCUMENTS

| | | |
|---|---|---|
| EP | 0 914 779 | 5/1999 |
| EP | 1504761 | 2/2005 |
| JP | 2007330124 | 12/2007 |
| WO | WO 94/15482 | 7/1994 |
| WO | WO 03/090759 | 11/2003 |
| WO | WO 2008/081795 | 7/2008 |
| WO | WO2008/084074 | 7/2008 |

OTHER PUBLICATIONS

"Barista Technique: Frothing Milk" [www.home-barista.com/espresso-guide-frothing-milk.html], printed on Sep. 7, 2011.
"Milk Composition" [www.milkfacts.info/Milk20%Composition/Milk%20Composition%20Page.htm], printed on Sep. 7, 2011.
Abrams SA, et al. "An Inulin-Type Fructan Enhances Calcium Absorption Primarily via an Effect on Colonic Absorption in Humans" *J Nutr* 2007; 137(10): 2208-12.

Benzie and Strain, "The reducing ability of plasma as a measure of 'antioxidant power'—the FRAP assay," *Analytical Biochemistry*, 1996; 239:70-76.
Bosscher D, et al. "Availabilities of calcium, iron, and zinc from dairy infant formulas is affected by soluble dietary fibers and modified starch fractions" *Nutrition* 2003; 19(7-8): 641-5.
Buettner, "Ascorbate autoxidation in the presence of iron and copper chelates," *Free Rad. Res. Comms.*, 1986, 1(6):349-353.
Charley PJ, et al. "Chelation of iron by sugars." *Biochim Biophys Acta* 1963; 69: 313-21.
Chen YC, Chen TC. "Mineral Utilization in Layers as Influenced by Dietary Oligofructose and Inulin." *Int J Poult Sci* 2004; 3(7): 442-5.
Coudray C, et al. "Effect of soluble or partly soluble dietary fibres supplementation on absorption and balance of calcium, magnesium, iron and zinc in healthy young men." *Eur J Clin Nutr* 1997; 51(6).
Coudray C, et al. "Dietary inulin intake and age can significantly affect intestinal absorption of calcium and magnesium in rats: a stable isotope approach." *Nutr J* 2005; 4: 29.
Demigne C, et al. "Effects of feeding fermentable carbohydrates on the cecal concentrations of minerals and their fluxes between the cecum and blood plasma in the rat." *J Nutr* 1989; 119(11): 1625-30.
Devareddy L, et al. "The effects of fructo-oligosaccharides in combination with soy protein on bone in osteopenic ovariectomized rats." *Menopause* 2006; 13(4): 692-9.
Fields M, et al. "Development of copper deficiency in rats fed fructose or starch: weekly measurements of copper indices in blood." *Proc Soc Exp Biol Med* 1986; 181(1): 120-4.
Fields M, et al. "Copper-carbohydrate interaction in maternal, fetal and neonate rat *Neurotoxicol Teratol.*" 1988; 10(6): 555-62.
Fields M, Lewis CG. "Dietary fructose but not starch is responsible for hyperlipidemia associated with copper deficiency in rats: effect of high-fat diet." *J Am Coll Nutr* 1999; 18(1): 83-7.
Forth W, Rummel W. "Iron absorption." *Physiol Rev* 1973; 53(3): 724-92.
Greger JL. "Nondigestible carbohydrates and mineral bioavailability." *J Nutr* 1999; 129(7 Suppl):1434S-5S.
Ivaturi R, Kies C. "Mineral balances in humans as affected by fructose, high fructose corn syrup and sucrose." *Plant Foods Hum Nutr* 1992; 42(2): 143-51.
Jacob A, Miles PM. "Intraluminal transport of iron from stomach to small-inestinal mucosa." *Br Med J* 1969; 4: 778-81.
Kruger MC, et al. "The effect of fructooligosaccharides with various degrees of polymerization on calcium bioavailability in the growing rat." *Exp Biol Med* (Maywood ) 2003; 228(6): 683-8.
Kuryl T, et al. "Chromium(III) propionate and dietary fructans supplementation stimulate erythrocyte glucose uptake and beta-oxidation in lymphocytes of rats." *Biol Trace Elem Res* 2006; 114(1-3): 237-48.

(Continued)

*Primary Examiner* — Mina Haghighatian
(74) *Attorney, Agent, or Firm* — Fish & Richardson P.C.

(57) ABSTRACT

This document provides complexes comprising a mineral-amino acid compound and a polysaccharide. For example, the document provides compositions containing such complexes and methods of making and using such complexes.

36 Claims, 6 Drawing Sheets

OTHER PUBLICATIONS

Levrat MA, et al. "High propionic acid fermentations and mineral accumulation in the cecum of rats adapted to different levels of inulin." *J Nutr* 1991; 121(11): 1730-7.

Milne DB, Nielsen FH. "The interaction between dietary fructose and magnesium adversely affects macromineral homeostasis in men." *J Am Coll Nutr* 2000; 19(1): 31-7.

Nzeusseu A, et al. "Inulin and fructo-oligosaccharides differ in their ability to enhance the density of cancellous and cortical bone in the axial and peripheral skeleton of growing rats." *Bone* 2006; 38(3): 394-9.

O'Dell BL. "Fructose and mineral metabolism." *Am J Clin Nutr* 1993; 58(5 Suppl): 771S-8S.

Ohta A, et al. "Dietary heme iron does not prevent postgastrectomy anemia but fructooligosaccharides improve bioavailability of heme iron in rats." *Int J Vitam Nutr Res* 1999; 69(5): 348-55.

Reiser S, et al. "Indices of copper status in humans consuming a typical American diet containing either fructose or starch." *Am J Clin Nutr* 1985; 42(2): 242-51.

Roberfroid MB. "Concepts in functional foods: the case of inulin and oligofructose." *J Nutr* 1999;129(7 Suppl): 1398S-401S.

Roberfroid MB., et al. "Dietary chicory inulin increases whole-body bone mineral density in growing male rats." *J Nutr* 2002; 132(12): 3599-602.

Scholfield DJ, et al. "Dietary copper, simple sugars, and metabolic changes in pigs." *J Nutr Biochem* 1990; 1(7): 362-8.

Seal CJ, Mathers JC. "Intestinal zinc transfer by everted gut sacs from rats given diets containing different amounts and types of dietary fibre." *Br J Nutr* 1989; 62(1): 151-63.

van den Heuvel EG, et al. "Oligofructose stimulates calcium absorption in adolescents" *Am J Clin Nutr*; 1999; 69(3): 544-8.

Wapnir RA, et al. "Zinc intestinal absorption: effect of carbohydrate." *Nutr Res* 1989; 9: 1277-84.

Wapnir RA, Devas G. "Copper deficiency: interaction with high-fructose and high-fat diets in rats." *Am J Clin Nutr* 1995; 61(1): 105-10.

Weaver CM. "Inulin, oligofructose and bone health: experimental approaches and mechanisms." *Br J Nutr* 2005; 93 Suppl 1: S99-103.

Younes H, et al. "Effects of two fermentable carbohydrates (inulin and resistant starch) and their combination on calcium and magnesium balance in rats." *Br J Nutr* 2001; 86(4): 479-85.

Authorized Officer Gijsbertus Beijer, International Preliminary Report on Patentability in PCT/US2009/050111, mailed Jan. 20, 2011, 8 pages.

Authorized Officer Bong Ho Chang, International Search Report in PCT/US09/050111, mailed Feb. 17, 2010, 5 pages.

European Search Report in European Application No. 09795189.1, dated Feb. 20, 2012, 10 pages.

* cited by examiner

MINERAL AMINO ACID POLYSACCHARIDE COMPLEX

CROSS-REFERENCE TO RELATED APPLICATIONS

This application claims priority to U.S. Provisional Application Ser. No. 61/079,176, filed on Jul. 9, 2008, which is incorporated by reference in its entirety herein.

TECHNICAL FIELD

This document relates to a complex comprising a mineral-amino acid compound and a polysaccharide, including compositions and methods of making and using such complexes.

BACKGROUND

Minerals are required as part of the human diet for good health. For example: calcium is a major component of bones and teeth; iron is an essential constituent of hemoglobin; copper, magnesium, and zinc are co-factors for a variety of enzymes; and manganese and selenium can function as antioxidants and contribute to endothelial integrity. Mineral deficiencies can lead to poor health and specific disorders. The human body requires traces of minerals, e.g., calcium, iron, copper, and zinc, in soluble form to provide metallic ions which are bioavailable within the bloodstream. With the increase in highly processed and convenience foods, however, there are concerns that the typical diet in today's conditions may not contain sufficient levels of such minerals.

Naturally occurring minerals found in foods are often chelated or bound within an organic matrix. Minerals found in dietary supplements, however, are often in the form of an inorganic salt, for example, as a mineral sulfate. These inorganic mineral species are more reactive and can catalyze production of free radicals, which have been associated with various degenerative diseases or conditions, within the digestive tract.

SUMMARY

This document provides complexes comprising a mineral-amino acid compound and a polysaccharide. For example, the document provides compositions containing such complexes and methods of making and using such complexes.

Provided herein is a complex prepared by a process including heating a composition comprising water, one or more mineral-amino acid compounds, and one or more polysaccharides at a temperature from about 100° F. to about 180° F., for example 160° F., to form said complex. In some cases, the process further includes drying the complex. In certain cases, the composition is heated for from about 5 minutes to about 30 minutes, for example, about 20 minutes.

In another aspect, a process of preparing a complex is provided. The process includes heating a composition comprising water, one or more mineral-amino acid compounds and one or more polysaccharides at a temperature from about 100° F. to about 180° F. to form the complex.

Further provided herein is a composition comprising two or more mineral-amino acid polysaccharide complexes. In some cases, the two or more mineral-amino acid polysaccharide complexes can be selected from the group consisting of a calcium amino acid polyfructose complex; iron amino acid polyfructose complex; iodine amino acid polyfructose complex; magnesium amino acid polyfructose complex; zinc amino acid polyfructose complex; selenium amino acid polyfructose complex; copper amino acid polyfructose complex; manganese amino acid polyfructose complex; molybdenum amino acid polyfructose complex; and boron amino acid polyfructose complex. In some cases, the composition further includes one or more of vitamin A; vitamin C; vitamin D; vitamin E; vitamin K; thiamin; riboflavin; niacin; vitamin B6; folate; vitamin B12; biotin; pantothenic acid; and phosphorous.

In one case, a daily dosage of the composition includes:
a. 1-5000 IU vitamin A;
b. 30-240 mg vitamin C;
c. 1-600 IU vitamin D;
d. 15-60 IU vitamin E;
e. 0-56 µg vitamin K;
f. 1.5-15 mg thiamin;
g. 1.7-17 mg riboflavin;
h. 20-100 mg niacin;
i. 2-20 mg vitamin B6;
j. 200-800 µg folate;
k. 6-18 µg vitamin B12;
l. 20-400 µg biotin;
m. 10-200 mg pantothenic acid;
n. 200-1000 mg calcium salt or complex;
o. 0-18 mg iron amino acid polyfructose complex;
p. 0-300 mg phosphorous;
q. 100-300 µg iodine amino acid polyfructose complex;
r. 100-400 mg magnesium salt or complex;
s. 5-30 mg zinc amino acid polyfructose complex;
t. 35-150 µg selenium amino acid polyfructose complex;
u. 1-5 mg copper amino acid polyfructose complex;
v. 1-5 mg manganese amino acid polyfructose complex;
w. 60-360 µg chromium amino acid polyfructose complex;
x. 50-150 µg molybdenum amino acid polyfructose complex; and
y. 0-300 µg boron amino acid polyfructose complex.

In certain cases, a daily dosage of the composition includes:
a. 3000 IU vitamin A;
b. 150 mg vitamin C;
c. 200 IU vitamin D;
d. 30 IU vitamin E;
e. 28 µg vitamin K;
f. 15 mg thiamin;
g. 17 mg riboflavin;
h. 75 mg niacin;
i. 10 mg vitamin B6;
j. 800 µg folate;
k. 12 µg vitamin B12;
l. 300 µg biotin;
m. 20 mg pantothenic acid;
n. 250 mg calcium salt or complex;
o. 9 mg iron amino acid polyfructose complex;
p. 65 mg phosphorous;
q. 150 µg iodine amino acid polyfructose complex;
r. 200 mg magnesium salt or complex;
s. 15 mg zinc amino acid polyfructose complex;
t. 105 µg selenium amino acid polyfructose complex;
u. 3 mg copper amino acid polyfructose complex;
v. 2.5 mg manganese amino acid polyfructose complex;
w. 120 µg chromium amino acid polyfructose complex;
x. 75 µg molybdenum amino acid polyfructose complex; and
y. 150 µg boron amino acid polyfructose complex.

In another case, a daily dosage of the composition includes:
a. 3000 IU vitamin A;
b. 150 mg vitamin C;
c. 200 IU vitamin D;
d. 30 IU vitamin E;

e. 15 mg thiamin;
f. 17 mg riboflavin;
g. 75 mg niacin;
h. 10 mg vitamin B6;
i. 600 μg folate;
j. 12 μg vitamin B12;
k. 60 μg biotin;
l. 20 mg pantothenic acid;
m. 250 mg calcium salt or complex;
n. 65 mg phosphorous;
o. 150 μg iodine amino acid polyfructose complex;
p. 200 mg magnesium salt or complex;
q. 15 mg zinc amino acid polyfructose complex;
r. 105 μg selenium amino acid polyfructose complex;
s. 3 mg copper amino acid polyfructose complex;
t. 4 mg manganese amino acid polyfructose complex;
u. 120 μg chromium amino acid polyfructose complex;
v. 75 μg molybdenum amino acid polyfructose complex; and
w. 150 μg boron amino acid polyfructose complex.

In some cases, a daily dosage of said composition includes:
a. 3000 IU vitamin A;
b. 150 mg vitamin C;
c. 200 IU vitamin D;
d. 30 IU vitamin E;
e. 8.5 mg thiamin;
f. 10 mg riboflavin;
g. 75 mg niacin;
h. 10 mg vitamin B6;
i. 1000 μg folate;
j. 16 μg vitamin B12;
k. 300 μg biotin;
l. 20 mg pantothenic acid;
m. 300 mg calcium salt or complex;
n. 9 mg iron amino acid polyfructose complex;
o. 65 mg phosphorous;
p. 150 μg iodine amino acid polyfructose complex;
q. 225 mg magnesium salt or complex;
r. 15 mg zinc amino acid polyfructose complex;
s. 105 μg selenium amino acid polyfructose complex;
t. 3 mg copper amino acid polyfructose complex;
u. 2.5 mg manganese amino acid polyfructose complex;
v. 120 μg chromium amino acid polyfructose complex;
w. 75 μg molybdenum amino acid polyfructose complex; and
x. 150 μg boron amino acid polyfructose complex.

In other cases, a daily dosage of said composition includes:
a. 2500 IU vitamin A;
b. 80 mg vitamin C;
c. 200 IU vitamin D;
d. 15 IU vitamin E;
e. 0.7 mg thiamin;
f. 0.8 mg riboflavin;
g. 9 mg niacin;
h. 1.05 mg vitamin B6;
i. 200 μg folate;
j. 3 μg vitamin B12;
k. 30 μg biotin;
l. 5 mg pantothenic acid;
m. 160 mg calcium salt or complex;
n. 5 mg iron amino acid polyfructose complex;
o. 20 mg phosphorous;
p. 70 μg iodine amino acid polyfructose complex;
q. 40 mg magnesium salt or complex;
r. 4 mg zinc amino acid polyfructose complex;
s. 0.5 mg copper amino acid polyfructose complex;
t. 0.5 mg manganese amino acid polyfructose complex;
u. 10 μg chromium amino acid polyfructose complex; and
v. 10 μg molybdenum amino acid polyfructose complex.

In certain cases, a daily dosage of said composition includes:
a. 5000 IU vitamin A;
b. 160 mg vitamin C;
c. 400 IU vitamin D;
d. 30 IU vitamin E;
e. 1.4 mg thiamin;
f. 1.6 mg riboflavin;
g. 18 mg niacin;
h. 2.1 mg vitamin B6;
i. 400 μg folate;
j. 6 μg vitamin B12;
k. 60 μg biotin;
l. 10 mg pantothenic acid;
m. 320 mg calcium salt or complex;
n. 10 mg iron amino acid polyfructose complex;
o. 40 mg phosphorous;
p. 140 μg iodine amino acid polyfructose complex;
q. 80 mg magnesium salt or complex;
r. 8 mg zinc amino acid polyfructose complex;
s. 1 mg copper amino acid polyfructose complex;
t. 1 mg manganese amino acid polyfructose complex;
u. 20 μg chromium amino acid polyfructose complex; and
v. 20 μg molybdenum amino acid polyfructose complex.

In other cases, a daily dosage of the composition includes:
a. 3500 IU vitamin A;
b. 150 mg vitamin C;
c. 200 IU vitamin D;
d. 45 IU vitamin E;
e. 7.5 mg thiamin;
f. 8.5 mg riboflavin;
g. 75 mg niacin;
h. 10 mg vitamin B6;
i. 600 μg folate;
j. 12 μg vitamin B12;
k. 60 μg biotin;
l. 15 mg pantothenic acid;
m. 250 mg calcium salt or complex;
n. 65 mg phosphorous;
o. 150 μg iodine amino acid polyfructose complex;
p. 200 mg magnesium salt or complex;
q. 15 mg zinc amino acid polyfructose complex;
r. 105 μg selenium amino acid polyfructose complex;
s. 3 mg copper amino acid polyfructose complex;
t. 3 mg manganese amino acid polyfructose complex;
u. 180 μg chromium amino acid polyfructose complex;
v. 90 μg molybdenum amino acid polyfructose complex; and
w. 150 μg boron amino acid polyfructose complex.

In some cases, a daily dosage of the composition includes:
a. 300 IU vitamin D;
b. 750 mg calcium salt or complex;
c. 100 mg phosphorous; and
d. 150 mg magnesium salt or complex.

In certain cases, a daily dosage of the composition includes:
a. 400 IU vitamin D;
b. 1000 mg calcium salt or complex;
c. 130 mg phosphorous; and
d. 200 mg magnesium salt or complex.

In other cases, a daily dosage of the composition includes:
a. 500 IU vitamin D;
b. 1250 mg calcium salt or complex;
c. 160 mg phosphorous; and
d. 250 mg magnesium salt or complex.

In any of the above a daily dosages of the composition, one or more of the calcium salt or complex and the magnesium salt or complex can include a corresponding mineral-amino acid polyfructose complex.

In one aspect, a complex comprising a mineral-amino acid compound and a polysaccharide is provided. The complex diffuses across a 3500 MW cutoff dialysis membrane slower than an uncomplexed mixture of the mineral-amino acid compound and the polysaccharide. In some cases, the mineral can be selected from the group consisting of Ca, Mg, K, Zn, Cu, Fe, I, Mn, Mo, Se, and Cr. In certain cases, the amino acid can be a natural amino acid such as L-alanine, L-arginine, L-asparagine, L-aspartic acid, L-cysteine, L-glutamic acid, L-glutamine, L-glycine, L-histidine, L-isoleucine, L-leucine, L-lysine, L-methionine, L-phenylalanine, L-proline, L-serine, L-threonine, L-tryptophan, L-tyrosine, L-valine, and mixtures thereof. In some cases, the polysaccharide can be selected from the group consisting of cellulose; polyhexoses; polypentoses; polydextrose; starch; polygalactan; polymannan; chitin; chitosan; chondroitin; polyfructose; inulin; pectin, and derivatives thereof. In certain cases, the polysaccharide is a cellulose derivative.

Also provided herein is a method for providing a mammal with a mineral having increased solubility. In some cases, the method includes administering the mineral, to the mammal, as a mineral-amino acid polysaccharide complex, thereby providing the mammal with the mineral in a form having greater solubility than the mineral administered as an inorganic salt. In certain cases, the increase in solubility occurs in the intestine of said mammal. In some cases, the mammal is a human. In other cases, the solubility of the mineral-amino acid polysaccharide complex is greater than the mineral administered as a mineral-amino acid.

This disclosure also provides a method for providing a mammal with a mineral and antioxidant mixture having reduced mineral-catalyzed oxidation. The method can include administering a composition comprising a mineral and an antioxidant, to the mammal, wherein the mineral is in the form of a mineral-amino acid polysaccharide complex, and wherein the rate of mineral-catalyzed oxidation within the mammal is lower than the rate of mineral-catalyzed oxidation when the mineral is administered as an inorganic salt. In some cases, the antioxidant is selected from the group consisting of ascorbic acid, tocopherols, carotenoids, lipoic acid, natural plant phenols and flavonoids, and polyunsaturated fatty acids. In other cases, the mineral is selected from the group consisting of Cu and Fe. In certain cases, the amino acid is a natural amino acid. For example, the amino acid can be selected from the group consisting of L-glycine and L-aspartic acid. In some instances, the polysaccharide is selected from the group consisting of cellulose; polyhexoses; polypentoses; polydextrose; starch; polygalactan; polymannan; chitin; chitosan; chondroitin; polyfructose; inulin; pectin, and derivatives thereof. For example, the polysaccharide can be inulin.

Further provided herein is a method for providing a mammal with a mineral having a reduced rate of free radical formation. The method can include administering the mineral, to the mammal, as a mineral-amino acid polysaccharide complex, thereby providing the mammal with the mineral in a form having a reduced rate of free radical formation as compared to administration of the mineral as an inorganic salt. In some cases, the free radical is a reactive oxygen species.

Unless defined otherwise, all technical and scientific terms used herein have the same meaning as is commonly understood by one of ordinary skill in the art to which this disclosure pertains. All patents, applications, published applications, and other publications are incorporated by reference in their entirety. In the event that there is a plurality of definitions for a term herein, those in this section prevail unless stated otherwise.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
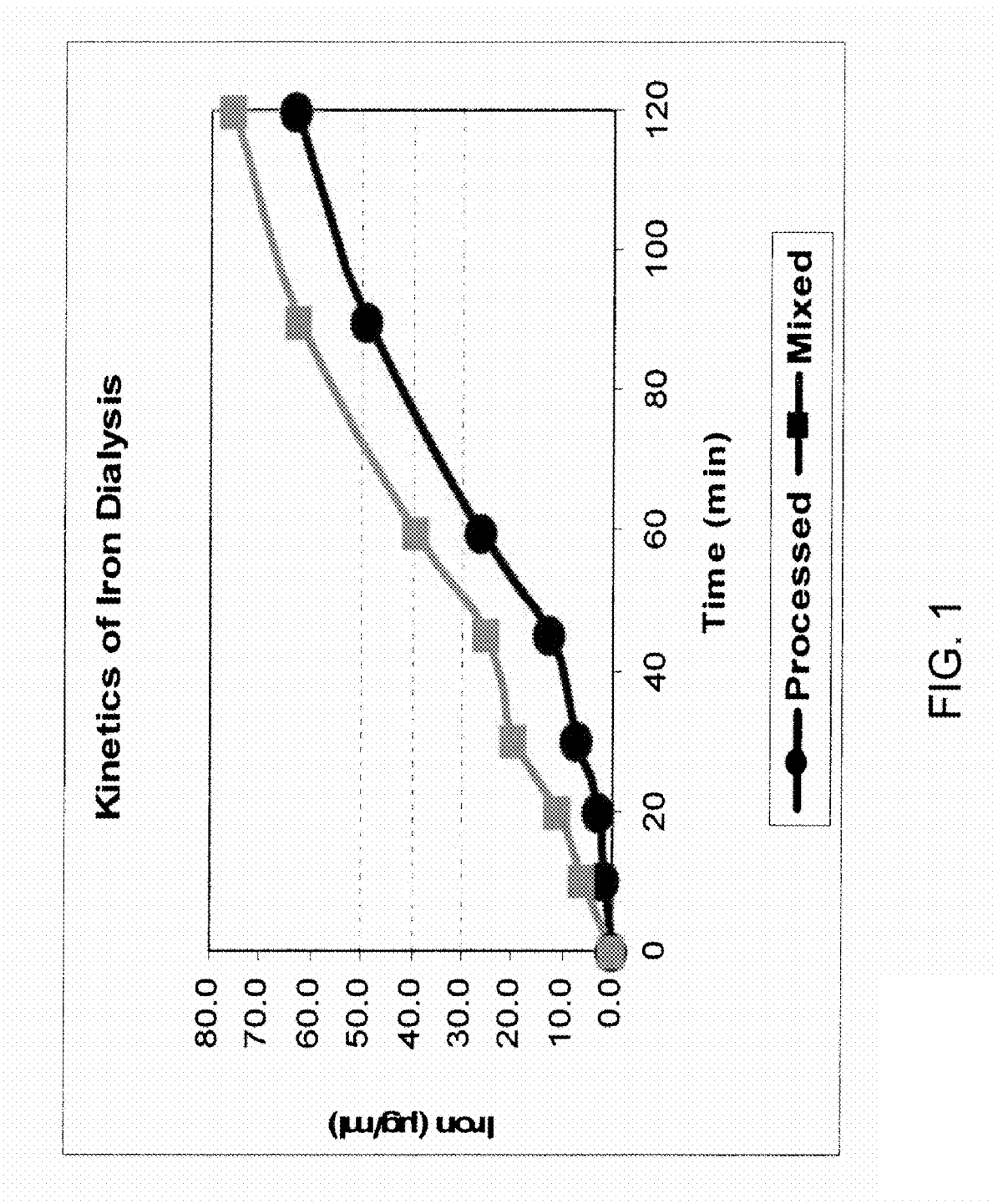
FIG. 1 is a line graph plotting iron concentration versus time for the rate of dialysis of various iron species.

This document provides a complex comprising a mineral-amino acid compound and a polysaccharide. For example, the document provides compositions containing such complexes and methods of making and using such complexes.

A complex, as described herein, comprises a mineral-amino acid compound and a polysaccharide. In some embodiments, the mineral-amino acid compound and the polysaccharide are conjugated. In some embodiments, the conjugation includes one or more of a covalent, coordinate covalent, Van der Waals interactions, hydrophobic, hydrogen, or ionic bond.

A mineral-amino acid compound can include any mineral having a dietary benefit that is chelated or complexed (e.g., forms a salt with) an amino acid. In some cases, the mineral-amino acid compound can be an amino acid chelated mineral. In some cases, the mineral-amino acid compound can be a mineral-amino acid complex or salt. Any mineral having a dietary or health benefit can be used in the complexes described herein. For example, chromium; calcium; copper; iron; magnesium; manganese; molybdenum; potassium; zinc; selenium; and iodine.

Any amino acid that can form a chelate or complex with a mineral can be used in the complexes described herein. In some cases, the amino acid portion of a mineral-amino acid compound can be one or more natural or unnatural amino acids. For example, an amino acid can be a natural amino acid. As used herein, the term "natural" amino acid refers to one of the twenty commonly occurring amino acids. Natural amino acids can be in their D or L form. For example, a natural amino acid can be selected from the group consisting of L-alanine, L-arginine, L-asparagine, L-aspartic acid, L-cysteine, L-glutamic acid, L-glutamine, L-glycine, L-histidine, L-isoleucine, L-leucine, L-lysine, L-methionine, L-phenylalanine, L-proline, L-serine, L-threonine, L-tryptophan, L-tyrosine, L-valine, and mixtures thereof. In some cases, an amino acid is selected from L-glycine and L-aspartic acid.

A polysaccharide can be any grouping of sugars (e.g., monosaccharides) linked together. For example, a polysaccharide can include cellulose derivatives. In some cases, a polysaccharide can include polyhexoses, polypentoses, and derivatives thereof In some cases, a polysaccharide can be selected from the group consisting of polydextrose, starch, polygalactan, polymannan, chitin, chitosan, chondroitin, polyfructose, pectin, and derivatives thereof. In some cases, a polysaccharide can be a polyfructose (e.g., inulin). In some cases, inulin can have a degree of polymerization ranging from about 2 to about 100 (e.g., about 2-10; about 12-15; about 20-30; about 25-45; about 30-40; about 50-75; about 45-65; about 50-55; about 70-80; about 75-90; and about 92-100).

A complex, as described herein, can be prepared by heating a composition comprising water, one or more mineral-amino acid compounds, and one or more polysaccharides at a temperature from about 100° F. to about 180° F. (e.g., 100° F.; 110° F.; 120° F.; 125° F.; 130° F.; 140° F.; 145° F.; 150° F.; 160° F.; 165° F.; 170° F.; 175° F.; and 180° F.). In some cases, the composition can be heated at from about 140° F. to about 180° F. In some cases, the composition can be heated at about 160° F. In some cases, the composition can be heated for from about 5 minutes to about 30 minutes (e.g., about 5 minutes; about 10 minutes; about 15 minutes; about 20 minutes; about 25 minutes; and about 30 minutes). In some cases, the composition can be heated for about 20 minutes. In some cases, the complex can be dried, for example, to a moisture content of less than about 15% (e.g., less than about 14%, less than about 12%, less than about 10%, less than about 8%, less than about 5%, and less than about 2%) following heating.

A complex can be prepared using a ratio of mineral-amino acid compound to polysaccharide ranging from 10:1 to 1:10 (e.g., 10:1; 6:1; 5:1; 4:1; 3:1; 2:1; 1:1.5; 1:1; 1:1.5; 1:2; 1:3; 1:4; 1:5; 1:6; and 1:10). For example, a ratio of mineral-amino acid compound to polysaccharide can be 5:1 or 1:1. In some cases, a mineral-amino acid polysaccharide complex can be zinc aspartate:zinc glycinate:inulin (degree of polymerization of 12-15) having a ratio of 50:30:20 by weight. In some cases, a mineral-amino acid polysaccharide complex can be iron aspartate:iron glycinate:inulin (degree of polymerization of 2-10) having a ratio of 25:25:50 by weight.

The complexes described herein can have properties that distinguish them from a simple mixture of the same mineral-amino acid compound and polysaccharide. For example, a complex of a mineral-amino acid compound and a polysaccharide can diffuse slower across a 3500 MW cutoff dialysis membrane then an uncomplexed mixture of the same mineral-amino acid compound and polysaccharide (see Example 2). The complex also can exhibit a different Fourier-Transform Near-IR (FT-NIR) spectrum compared to a similar uncomplexed mixture as determined by an industry standard correlation factor (see Example 3).

This disclosure also provides for a composition comprising two or more complexes as described herein. For example, a composition can comprise two or more of a calcium-amino acid polysaccharide complex; iron-amino acid polysaccharide complex; iodine-amino acid polysaccharide complex; magnesium-amino acid polysaccharide complex; zinc-amino acid polysaccharide complex; selenium-amino acid polysaccharide complex; copper-amino acid polysaccharide complex; manganese-amino acid polysaccharide complex; molybdenum-amino acid polysaccharide complex; and boron-amino acid polysaccharide complex. In some cases, the mineral-amino acid polysaccharide complex can include a mineral-amino acid compound comprising 75% aspartate and 25% glycinate. In some cases, the mineral-amino acid polysaccharide complex can include polyfructose. In some cases, the mineral-amino acid polysaccharide complex can include inulin having a degree of polymerization ranging from about 2 to about 100. In some cases, the mineral-amino acid polysaccharide complexes can include inulin having a degree of polymerization of about 12-15.

In some cases, the composition can also include one or more of vitamin A; vitamin C; vitamin D; vitamin E; vitamin K; thiamin; riboflavin; niacin; vitamin B6; folate; vitamin B12; biotin; pantothenic acid; and phosphorous.

In some cases, a composition can comprise:

|  | Total Daily Dose |
|---|---|
| Vitamin A (as beta carotene) | 1-5000 IU |
| Vitamin C (as ascorbic acid) | 30-240 mg |
| Vitamin D (as cholecalciferol) | 1-600 IU |
| Vitamin E (as d-alpha tocopheryl succinate) | 15-60 IU |
| Vitamin K (as phytonadione) | 0-56 µg |
| Thiamin (as thiamin HCl) | 1.5-15 mg |
| Riboflavin | 1.7-17 mg |
| Niacin (as niacinamide) | 20-100 mg |
| Vitamin B6 (as pyridoxine HCl) | 2-20 mg |
| Folate (as folic acid) | 200-800 µg |
| Vitamin B12 (as cyanocobalamin) | 6-18 µg |
| Biotin (as d-biotin) | 20-400 µg |
| Pantothenic Acid (as calcium pantothenate) | 10-200 mg |
| Calcium (as calcium carbonate, dicalcium phosphate, calcium citrate, calcium gluconate, calcium amino acid polysaccharide complex) | 200-1000 mg |
| Iron (as iron amino acid polysaccharide complex) | 0-18 mg |
| Phosphorous (as dicalcium phosphate) | 0-300 mg |
| Iodine (as iodine amino acid polysaccharide complex) | 100-300 µg |
| Magnesium (as magnesium oxide, magnesium lactate, magnesium citrate, magnesium amino acid polysaccharide complex) | 100-400 mg |
| Zinc (zinc amino acid polysaccharide complex) | 5-30 mg |
| Selenium (as selenium amino acid polysaccharide complex) | 35-150 µg |
| Copper (copper amino acid polysaccharide complex) | 1-5 mg |

-continued

|  | Total Daily Dose |
|---|---|
| Manganese (as manganese amino acid polysaccharide complex) | 1-5 mg |
| Chromium (as chromium amino acid polysaccharide complex) | 60-360 µg |
| Molybdenum (as molybdenum amino acid polysaccharide complex) | 50-150 µg |
| Boron (as boron amino acid polysaccharide complex) | 0-300 µg |

The phrase "total daily dose" as used herein refers to the amount of active ingredient administered over a 24 hour period. For example, the amount of zinc amino acid polysaccharide complex in a total daily dose is calculated based on the amount of zinc administered over 24 hours, not on the amount of zinc amino acid polysaccharide complex administered over 24 hours. A total daily dose may be prepared and administered in the form of one or more tablets (e.g., two tablets, three tablets, four tablets, five tablets, and six tablets). In some cases, the one or more tablets can be administered in one or more dosages over the course of 24 hours (e.g., one dose, two doses, three doses, four doses, five doses, and six doses), wherein the one or more dosages do not exceed the total daily dose.

In some cases, a composition can be:

|  | Total Daily Dose |
|---|---|
| Vitamin A (as beta carotene) | 3000 IU |
| Vitamin C (as ascorbic acid) | 150 mg |
| Vitamin D (as cholecalciferol) | 200 IU |
| Vitamin E (as d-alpha tocopheryl succinate) | 30 IU |
| Vitamin K (as phytonadione) | 28 µg |
| Thiamin (as thiamin HCl) | 15 mg |
| Riboflavin | 17 mg |
| Niacin (as niacinamide) | 75 mg |
| Vitamin B6 (as pyridoxine HCl) | 10 mg |
| Folate (as folic acid) | 800 µg |
| Vitamin B12 (as cyanocobalamin) | 12 µg |
| Biotin (as d-biotin) | 300 µg |
| Pantothenic Acid (as calcium pantothenate) | 20 mg |
| Calcium (as calcium carbonate, dicalcium phosphate, calcium citrate, calcium gluconate, calcium amino acid polyfructose complex) | 250 mg |
| Iron (as iron amino acid polyfructose complex) | 9 mg |
| Phosphorous (as dicalcium phosphate) | 65 mg |
| Iodine (as iodine amino acid polyfructose complex) | 150 µg |
| Magnesium (as magnesium oxide, magnesium lactate, magnesium citrate, magnesium amino acid polyfructose complex) | 200 mg |
| Zinc (zinc amino acid polyfructose complex) | 15 mg |
| Selenium (as selenium amino acid polyfructose complex) | 105 µg |
| Copper (copper amino acid polyfructose complex) | 3 mg |
| Manganese (as manganese amino acid polyfructose complex) | 2.5 mg |
| Chromium (as chromium amino acid polyfructose complex) | 120 µg |
| Molybdenum (as molybdenum amino acid polyfructose complex) | 75 µg |
| Boron (as boron amino acid polyfructose complex) | 150 µg |

In some cases, a composition can be:

|  | Total Daily Dose |
|---|---|
| Vitamin A (as beta carotene) | 3000 IU |
| Vitamin C (as ascorbic acid) | 150 mg |
| Vitamin D (as cholecalciferol) | 200 IU |

-continued

|  | Total Daily Dose |
|---|---|
| Vitamin E (as d-alpha tocopheryl succinate) | 30 IU |
| Thiamin (as thiamin HCl) | 15 mg |
| Riboflavin | 17 mg |
| Niacin (as niacinamide) | 75 mg |
| Vitamin B6 (as pyridoxine HCl) | 10 mg |
| Folate (as folic acid) | 600 µg |
| Vitamin B12 (as cyanocobalamin) | 12 µg |
| Biotin (as d-biotin) | 60 µg |
| Pantothenic Acid (as calcium pantothenate) | 20 mg |
| Calcium (as calcium carbonate, dicalcium phosphate, calcium citrate, calcium gluconate, calcium amino acid polyfructose complex) | 250 mg |
| Phosphorous (as dicalcium phosphate) | 65 mg |
| Iodine (as iodine amino acid polyfructose complex) | 150 µg |
| Magnesium (as magnesium oxide, magnesium lactate, magnesium citrate, magnesium amino acid polyfructose complex) | 200 mg |
| Zinc (zinc amino acid polyfructose complex) | 15 mg |
| Selenium (as selenium amino acid polyfructose complex) | 105 µg |
| Copper (copper amino acid polyfructose complex) | 3 mg |
| Manganese (as manganese amino acid polyfructose complex) | 4 mg |
| Chromium (as chromium amino acid polyfructose complex) | 120 µg |
| Molybdenum (as molybdenum amino acid polyfructose complex) | 75 µg |
| Boron (as boron amino acid polyfructose complex) | 150 µg |

In some cases, a composition can be:

|  | Total Daily Dose |
|---|---|
| Vitamin A (as beta carotene) | 3000 IU |
| Vitamin C (as ascorbic acid) | 150 mg |
| Vitamin D (as cholecalciferol) | 200 IU |
| Vitamin E (as d-alpha tocopheryl succinate) | 30 IU |
| Thiamin (as thiamin HCl) | 8.5 mg |
| Riboflavin | 10 mg |
| Niacin (as niacinamide) | 75 mg |
| Vitamin B6 (as pyridoxine HCl) | 10 mg |
| Folate (as folic acid) | 1000 µg |
| Vitamin B12 (as cyanocobalamin) | 16 µg |
| Biotin (as d-biotin) | 300 µg |
| Pantothenic Acid (as calcium pantothenate) | 20 mg |
| Calcium (as calcium carbonate, dicalcium phosphate, calcium citrate, calcium gluconate, calcium amino acid polyfructose complex) | 300 mg |
| Iron (as iron amino acid polyfructose complex) | 9 mg |
| Phosphorous (as dicalcium phosphate) | 65 mg |
| Iodine (as iodine amino acid polyfructose complex) | 150 µg |
| Magnesium (as magnesium oxide, magnesium lactate, magnesium citrate, magnesium amino acid polyfructose complex) | 225 mg |
| Zinc (zinc amino acid polyfructose complex) | 15 mg |
| Selenium (as selenium amino acid polyfructose complex) | 105 µg |
| Copper (copper amino acid polyfructose complex) | 3 mg |

-continued

| | Total Daily Dose |
|---|---|
| Manganese (as manganese amino acid polyfructose complex) | 2.5 mg |
| Chromium (as chromium amino acid polyfructose complex) | 120 µg |
| Molybdenum (as molybdenum amino acid polyfructose complex) | 75 µg |
| Boron (as boron amino acid polyfructose complex) | 150 µg |

In some cases, a composition can be:

| | Total Daily Dose |
|---|---|
| Vitamin A (as beta carotene) | 2500 IU |
| Vitamin C (as ascorbic acid) | 80 mg |
| Vitamin D (as cholecalciferol) | 200 IU |
| Vitamin E (as d-alpha tocopheryl succinate) | 15 IU |
| Thiamin (as thiamin HCl) | 0.7 mg |
| Riboflavin | 0.8 mg |
| Niacin (as niacinamide) | 9 mg |
| Vitamin B6 (as pyridoxine HCl) | 1.05 mg |
| Folate (as folic acid) | 200 µg |
| Vitamin B12 (as cyanocobalamin) | 3 µg |
| Biotin (as d-biotin) | 30 µg |
| Pantothenic Acid (as calcium pantothenate) | 5 mg |
| Calcium (as calcium carbonate, dicalcium phosphate, calcium citrate, calcium gluconate, calcium amino acid polyfructose complex) | 160 mg |
| Iron (as iron amino acid polyfructose complex) | 5 mg |
| Phosphorous (as dicalcium phosphate) | 20 mg |
| Iodine (as iodine amino acid polyfructose complex) | 70 µg |
| Magnesium (as magnesium oxide, magnesium lactate, magnesium citrate, magnesium amino acid polyfructose complex) | 40 mg |
| Zinc (zinc amino acid polyfructose complex) | 4 mg |
| Copper (copper amino acid polyfructose complex) | 0.5 mg |
| Manganese (as manganese amino acid polyfructose complex) | 0.5 mg |
| Chromium (as chromium amino acid polyfructose complex) | 10 µg |
| Molybdenum (as molybdenum amino acid polyfructose complex) | 10 µg |

In some cases, a composition can be:

| | Total Daily Dose |
|---|---|
| Vitamin A (as beta carotene) | 5000 IU |
| Vitamin C (as ascorbic acid) | 160 mg |
| Vitamin D (as cholecalciferol) | 400 IU |
| Vitamin E (as d-alpha tocopheryl succinate) | 30 IU |
| Thiamin (as thiamin HCl) | 1.4 mg |
| Riboflavin | 1.6 mg |
| Niacin (as niacinamide) | 18 mg |
| Vitamin B6 (as pyridoxine HCl) | 2.1 mg |
| Folate (as folic acid) | 400 µg |
| Vitamin B12 (as cyanocobalamin) | 6 µg |
| Biotin (as d-biotin) | 60 µg |
| Pantothenic Acid (as calcium pantothenate) | 10 mg |
| Calcium (as calcium carbonate, dicalcium phosphate, calcium citrate, calcium gluconate, calcium amino acid polyfructose complex) | 320 mg |
| Iron (as iron amino acid polyfructose complex) | 10 mg |
| Phosphorous (as dicalcium phosphate) | 40 mg |
| Iodine (as iodine amino acid polyfructose complex) | 140 µg |
| Magnesium (as magnesium oxide, magnesium lactate, magnesium citrate, magnesium amino acid polyfructose complex) | 80 mg |
| Zinc (zinc amino acid polyfructose complex) | 8 mg |

-continued

| | Total Daily Dose |
|---|---|
| Copper (copper amino acid polyfructose complex) | 1 mg |
| Manganese (as manganese amino acid polyfructose complex) | 1 mg |
| Chromium (as chromium amino acid polyfructose complex) | 20 µg |
| Molybdenum (as molybdenum amino acid polyfructose complex) | 20 µg |

In some cases, a composition can be:

| | Total Daily Dose |
|---|---|
| Vitamin A (as beta carotene) | 3500 IU |
| Vitamin C (as ascorbic acid) | 150 mg |
| Vitamin D (as cholecalciferol) | 200 IU |
| Vitamin E (as d-alpha tocopheryl succinate) | 45 IU |
| Thiamin (as thiamin HCl) | 7.5 mg |
| Riboflavin | 8.5 mg |
| Niacin (as niacinamide) | 75 mg |
| Vitamin B6 (as pyridoxine HCl) | 10 mg |
| Folate (as folic acid) | 600 µg |
| Vitamin B12 (as cyanocobalamin) | 12 µg |
| Biotin (as d-biotin) | 60 µg |
| Pantothenic Acid (as calcium pantothenate) | 15 mg |
| Calcium (as calcium carbonate, dicalcium phosphate, calcium citrate, calcium gluconate, calcium amino acid polyfructose complex) | 250 mg |
| Phosphorous (as dicalcium phosphate) | 65 mg |
| Iodine (as iodine amino acid polyfructose complex) | 150 µg |
| Magnesium (as magnesium oxide, magnesium lactate, magnesium citrate, magnesium amino acid polyfructose complex) | 200 mg |
| Zinc (zinc amino acid polyfructose complex) | 15 mg |
| Selenium (as selenium amino acid polyfructose complex) | 105 µg |
| Copper (copper amino acid polyfructose complex) | 3 mg |
| Manganese (as manganese amino acid polyfructose complex) | 3 mg |
| Chromium (as chromium amino acid polyfructose complex) | 180 µg |
| Molybdenum (as molybdenum amino acid polyfructose complex) | 90 µg |
| Boron (as boron amino acid polyfructose complex) | 150 µg |

In some cases, a composition can be:

| | Total Daily Dose |
|---|---|
| Vitamin D (as cholecalciferol) | 300 IU |
| Calcium (as calcium carbonate, dicalcium phosphate, calcium citrate, calcium gluconate, calcium amino acid polyfructose complex) | 750 mg |
| Phosphorous (as dicalcium phosphate) | 100 mg |
| Magnesium (as magnesium oxide, magnesium lactate, magnesium citrate, magnesium amino acid polyfructose complex) | 150 mg |

In some cases, a composition can be:

|  | Total Daily Dose |
| --- | --- |
| Vitamin D (as cholecalciferol) | 400 IU |
| Calcium (as calcium carbonate, dicalcium phosphate, calcium citrate, calcium gluconate, calcium amino acid polyfructose complex) | 1000 mg |
| Phosphorous (as dicalcium phosphate) | 130 mg |
| Magnesium (as magnesium oxide, magnesium lactate, magnesium citrate, magnesium amino acid polyfructose complex) | 200 mg |

In some cases, a composition can be:

|  | Total Daily Dose |
| --- | --- |
| Vitamin D (as cholecalciferol) | 200 IU |
| Calcium (as calcium carbonate, dicalcium phosphate, calcium citrate, calcium gluconate, calcium amino acid polyfructose complex) | 500 mg |
| Phosphorous (as dicalcium phosphate) | 64 mg |
| Magnesium (as magnesium oxide, magnesium lactate, magnesium citrate, magnesium amino acid polyfructose complex) | 100 mg |

In some cases, a composition can be:

|  | Total Daily Dose |
| --- | --- |
| Vitamin D (as cholecalciferol) | 500 IU |
| Calcium (as calcium carbonate, dicalcium phosphate, calcium citrate, calcium gluconate, calcium amino acid polyfructose complex) | 1250 mg |
| Phosphorous (as dicalcium phosphate) | 160 mg |
| Magnesium (as magnesium oxide, magnesium lactate, magnesium citrate, magnesium amino acid polyfructose complex) | 250 mg |

A mineral-amino acid polysaccharide complex, as described herein, can reduce the formation of free radicals in the intestinal tract as compared to an uncomplexed mineral (e.g., a mineral sulfate, chloride, citrate, or gluconate). In some instances, the mineral-amino acid polysaccharide complex can be an iron-amino acid polyfructose complex or a copper-amino acid polyfructose complex. In some instances, the mineral-amino acid polysaccharide complex can be a glycinate or aspartic acid-iron or copper species complexed with inulin. In some instances, the uncomplexed mineral can be an inorganic salt (e.g., a mineral sulfate, chloride or oxide). Reduction in the formation of free radicals can include reduction in the formation of reactive oxygen species (ROS) such as hydroxyl radical, peroxide, and superoxide radical. ROS can initiate radical chain reactions within the body. For example, an uncomplexed mineral provided in a dietary supplement can catalyze the formation of ROS that can oxidize one or more antioxidants from the dietary supplement (e.g., ascorbic acid, tocopherols, carotenoids, lipoic acid, natural plant phenols and flavonoids, and polyunsaturated fatty acids). Without being bound by theory, a complexed mineral, however, is thought to be protected by the amino acid and/or the polysaccharide and thus is less able to catalyze free radical formation. When administered in the form of a dietary supplement, a reduction in the formation of free radicals can decrease the oxidation of any antioxidants present in the dietary supplement itself.

Accordingly, further provided herein is a method for providing a mammal with a mineral and antioxidant mixture with reduced mineral-catalyzed oxidation. In some instances, the method includes administering to the mammal a composition comprising a mineral and an antioxidant, wherein the mineral is in the form of a mineral-amino acid polysaccharide complex, as described herein. The mineral-amino acid polysaccharide complex can exhibit reduced mineral-catalyzed oxidation of the antioxidant compared to an uncomplexed mineral or a mineral administered as an inorganic salt. In some instances, the reduced rate of oxidation occurs in the intestine of the mammal.

Beyond stabilization of antioxidants present in a dietary supplement, a reduction in the formation of free radicals can also reduce oxidation of bio-molecules such as lipids, proteins, and DNA. In some cases oxidative damage of bio-molecules can lead to formation of many different intermediate radicals including toxic and/or pathogenic products. These radical species can change the structure and/or function of bio-molecules and can provoke some degenerative diseases (e.g., inflammation, cancer, and arteriosclerosis)

This disclosure provides methods for reducing formation of a free radical, reducing the amount of a free radical, and decreasing antioxidant oxidation in a mammal or cell using a complex as described herein (see Examples 4-6, 20, and 21). For example, a complex can be an amino acid-iron or copper compound complexed with a polysaccharide. In some cases, the cell is an intestinal cell. In some instances, the reduced formation of free radicals, reduced amount of free radicals, and decreased antioxidant oxidation occurs in the mammal's intestine.

In some cases, the methods can be used in vitro, for example, reducing free radical formation, reducing the amount of a free radical, or decreasing antioxidant reduction, can be performed by contacting a cell with a complex as described herein. The contacting can be performed in the presence of cells, wherein, optionally, a free radical or an antioxidant is present within the cells, or alternatively may be performed in a cell free medium. Uses of such in vitro methods of reducing formation of a free radical include, but are not limited to, use in a screening assay (for example, wherein the amino acid-iron or copper compound is used as a positive control or standard compared to compounds of unknown activity or potency in reducing formation of a free radical).

In some cases, the methods can be used in vivo, for example, reducing free radical formation, reducing the amount of a free radical, or decreasing antioxidant oxidation, can be performed by contacting a cell, in vivo, with a complex as described herein. The contacting can be achieved by causing the complex (e.g., an amino acid iron or copper species complexed with a polysaccharide) to be present in a mammal in an effective amount to, for example, reduce free radical formation. This can be achieved, for example, by administering an effective amount of the complex to the mammal, or by administering a composition comprising the complex to the mammal.

Uses of such in vivo methods of reducing free radical formation and the amount of a free radical include, but are not limited to, use in methods of treating or preventing a disease or condition such as a degenerative disease (e.g., inflammation, cancer, and arteriosclerosis). In some cases, an antioxidant can be selected from ascorbic acid, tocopherols, carotenoids, lipoic acid, natural plant phenols and flavonoids, and polyunsaturated fatty acids.

A mineral-amino acid polysaccharide complex, as described herein also has increased solubility at neutral pH as compared to an uncomplexed mineral (see Example 23). In some instances, the neutral pH occurs in the intestinal tract. Without being bound by theory, such increased solubility can increase the concentration of mineral absorbed by the body following administration.

EXAMPLES

Example 1

Preparation of Zinc-Amino Acid Inulin Complex 100 g of zinc aspartate and 50 g of zinc glycinate were mixed with 150 g of inulin (degree of polymerization 12-15). 60 mL of water was added. The mixture was heated up to 140° F. with stirring for 30 minutes. The mixture was then transferred onto a drying tray and was dried overnight or until the composition reached a moisture content of 8%.

Example 2

Dialysis Model

Equal weight samples of iron(II) bis-glycinate (10.1% Fe) and inulin (degree of polymerization of 12-15) were mixed with water. The mixture was shaken for 3 minutes until reagents dissolved completely. The solution was then diluted with water to a final concentration of 2 mg/mL. 5 mL of this solution was then transferred into a dialysis tube (Fisherbrand® regenerated cellulose, molecular weight cutoff=3,500) and allowed to sit for 5 minutes prior to starting dialysis. Dialysis against 100 mL of water was performed with slow agitation. Aliquots were taken every 10-15 minutes over the course of 2 hours. Iron(II) concentration was determined calorimetrically, using the reaction of 2,4,6-tri-(2-pyridyl)-s-tirazine (TPTZ) and $FeSO_4$ as a reference standard (see Benzie I. F. and Strain, J. J. *Anal. Biochem.* 1996; 239:70-6).

A sample of iron(II) bis-glycinate, processed with an equal weight of inulin (4.73% Fe) to prepare an iron(II) glycinate inulin complex was prepared (see Example 1) and dialyzed the same way.

Table 1 and FIG. 1 detail the concentration of iron(II) (µg/mL) in the dialysis solution for both samples at various time points.

TABLE 1

| Dialysis time (min) | Mixed | Processed |
|---|---|---|
| 0 | 0.0 | 0.0 |
| 10 | 5.9 | 1.4 |
| 20 | 11.1 | 2.6 |
| 30 | 19.9 | 7.1 |
| 45 | 25.0 | 12.7 |
| 60 | 39.0 | 25.9 |
| 90 | 62.7 | 49.0 |
| 120 | 75.9 | 63.3 |

A smaller amount of the iron-amino acid inulin complex penetrated through the membrane at all time points compared with the simple mixture (Table 1 and FIG. 1). These results indicated that the complex was a larger species and not formed simply upon mixture of the components.

Example 3

FT-NIR Model

Figure 2:
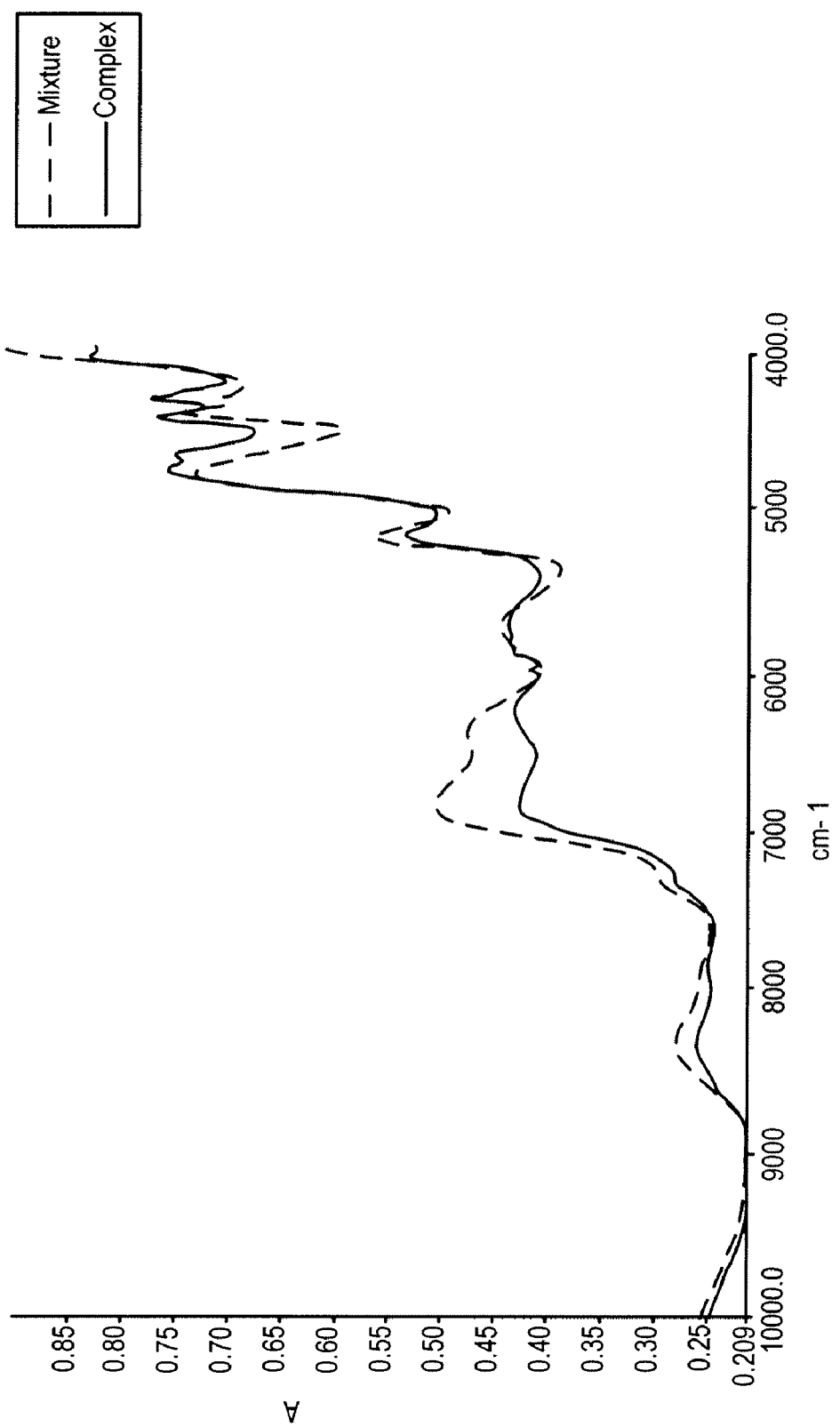
FIG. 2 is a line graph of absorbance versus inverse wavelength for the FT-NIR spectrum of a manganese aspartate complexed with inulin and a simple mixture of manganese aspartate and inulin.

Fourier Transformed (FT) Near Infrared spectrometry was performed on a Spectrum One NTS V.N3 (Perkin Elmer). A manganese aspartate inulin complex was prepared using a 1:1 weight ratio of mineral-amino acid compound to inulin (see Example 1). Dry manganese aspartate was combined with an equal weight of inulin powder, and the mixture was gently agitated to obtain a homogeneous powder that was used as a control (see FIG. 2).

The complex and mixture failed the identity test based on an industry standard calculated correlation factor. Correlation–0.886 (pass>0.95); Factor–0.679 (pass>0.95). In addition, visually, both FT-NIR spectra displayed different intensities in some areas of the spectrum. In particular, new peaks were observed in the spectrum of the complexed sample.

These results indicate that the complexed sample and the simple mixture are different chemical entities.

Example 4

Ascorbyl Radical Kinetics

Samples of iron(II) sulfate, iron(II) bis-glycinate (FeAAC), and an iron(II) bis-glycinate inulin complex (FeAAC/OF; ratio 1:10 w/w) were analyzed using EPR spectroscopy to determine their ability to generate the ascorbate radical, i.e. to catalyze ascorbic oxidation. The samples were dissolved in 10 mM HEPES buffer (pH 7.2) to a final concentration 0.9 mM of iron. Ascorbic acid was dissolved in the same buffer at a concentration of 4.04 mM.

The iron solutions were mixed with the ascorbic acid solution, and the mixture was transferred into capillary tubes for measurement. Multiple readings were performed over 30 minutes.

EPR measurements were performed in 50 µL capillary tubes at room temperature using a Bruker ER-200 X-band EPR spectrometer. Instrumental conditions included: a microwave frequency of 9.71 GHz; a center field of 3472 G; a scan range of 10 G; a scan time of 20 seconds; a modulation value of 1.25 G; a time constant of 0.5 seconds; a microwave power of 10 mW; and an instrumental gain of $2 \times 10^6$.

The relative amplitudes of the ascorbyl radical signal, which can be correlated to the concentration of ascorbyl radical present in the solution, were measured (Table 2).

TABLE 2

| Time (min) | $FeSO_4$ | FeAAC | FeAAC/OF |
|---|---|---|---|
| 1.5 | 100% | 100% | 100% |
| 3.5 | 76% | 74% | — |
| 5.5 | 64% | 65% | 80% |
| 10.0 | 24% | 47% | 79% |
| 14.0 | 14% | 33% | 69% |
| 20.0 | 10% | 19% | 63% |
| 28.0 | 5% | 19% | 61% |

The ascorbyl radical was stabilized for a longer period of time when the reaction was catalyzed by iron glycinate, compared with the iron sulfate (Table 2). Moreover, the iron glycinate inulin complex increased the lifetime of the ascorbyl radical by an even greater degree.

Example 5

Hydroxyl Radical Formation

The rate of hydroxyl radical formation catalyzed by a complex comprising an iron- or copper-amino acid inulin complex was compared to the iron- or copper-amino acid compound alone.

Mineral (Cu or Fe) was dissolved in 10 mM HEPES buffer (pH 7.2) containing DMPO. Iron and copper were used in the form of amino acid compounds (i.e., glycinates; AAC) and as amino acid inulin complexes (1:9 w/w; AAC/OF). Hydrogen peroxide was added 90 seconds prior to measurement. The final composition of the reaction mixture was metal—800 µM, DMPO—18.7 mM, and $H_2O_2$—61 mM.

The spin trapping reagent—5,5-dimethylpyrroline-N-oxide (DMPO) was used for monitoring hydroxyl radical. EPR conditions were: a microwave frequency of 9.71 GHz; a center field of 3472 G; a scan range of 100 G; a scan time of 100 seconds; a modulation value of 1.25 G; a time constant of 0.5 seconds; a microwave power of 10 mW; and an instrumental gain of $2\times10^6$.

The relative signal amplitudes for DMPO/hydroxyl radical adduct, which can be correlated to the concentration of hydroxyl radical present in the solution, was measured (Table 3).

TABLE 3

|    | AAC  | AAC/OF |
|----|------|--------|
| Fe | 100% | 36%    |
| Cu | 100% | 50%    |

The mineral-amino acid inulin complexes exhibited a decreased rate of hydroxyl radical formation compared to the mineral-amino acid compound alone (Table 3).

Example 6

Ability of Different Forms of Copper to Catalyze Oxidation of DCF

The rate at which various forms of copper catalyze the oxidation of DCF (2',7'-Dichlorodihydrofluorescein) was studied using copper sulfate, a copper gluconate inulin complex (AAOC), and copper gluconate. Solutions of all copper samples were prepared in 20 mM HEPES buffer (pH 7.2) with a concentration of 25 µM. A DCF stock solution prepared in 20 mM NaOH to provide hydrolysis of acetates. The DCF stock solution was diluted in 20 mM HEPES buffer (pH 7.2) to concentration of 0.1 mM. 0.5 mL of each copper solution was mixed with 1 mL of DCF solution. The reaction was initiated by addition of 0.1 mL of 0.1% hydrogen peroxide. Oxidation of DCF was monitored by measuring its optical density at 500 nm.

Figure 3:
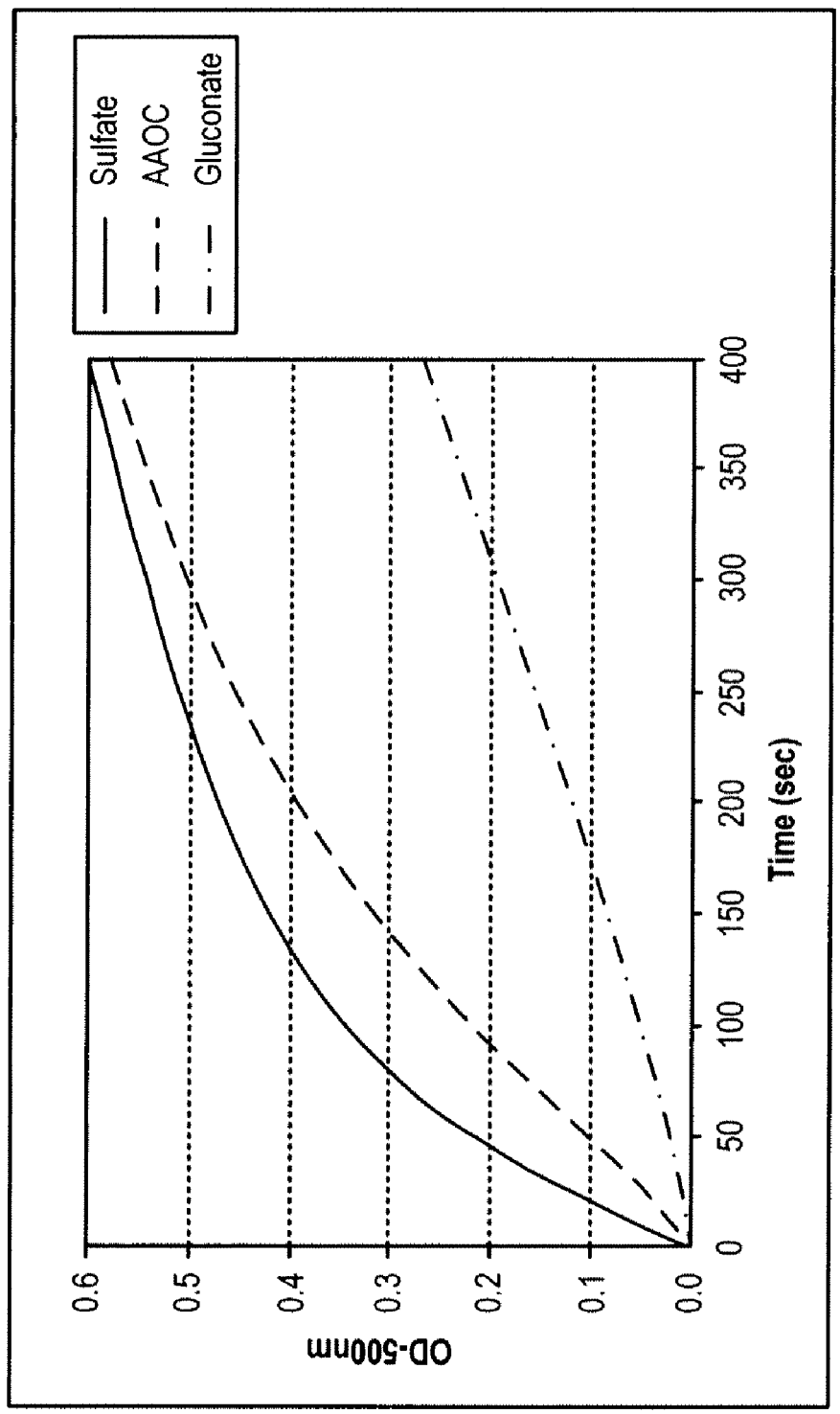
FIG. 3 is a line graph of optical density at 500 nm versus time (seconds) for the kinetics of 2',7'-Dichlorodihydrofluorescein oxidation.

The copper-amino acid inulin complex exhibited the slowest rate of DCF oxidation compared to the copper-amino acid compound and copper sulfate species (FIG. 3).

Example 7

Dietary Supplement Formulation

A dietary supplement formulation was prepared using mineral-amino acid polyfructose complexes, specifically mineral-(25:75 glycinate:aspartate) inulin complexes. The formulation was prepared by combining the components listed below in Table 4 with appropriate excipients. The combined formulation was then pressed into tablets (the daily dosage provided in Table 4 represents the amount in three tablets).

TABLE 4

|   | Daily Dosage |
|---|---|
| Vitamin A (as beta carotene) | 3000 IU |
| Vitamin C (as ascorbic acid) | 150 mg |
| Vitamin D (as cholecalciferol) | 200 IU |
| Vitamin E (as d-alpha tocopheryl succinate) | 30 IU |
| Vitamin K (as phytonadione) | 28 µg |
| Thiamin (as thiamin HCl) | 15 mg |
| Riboflavin | 17 mg |
| Niacin (as niacinamide) | 75 mg |
| Vitamin B6 (as pyridoxine HCl) | 10 mg |
| Folate (as folic acid) | 800 µg |
| Vitamin B12 (as cyanocobalamin) | 12 µg |
| Biotin (as d-biotin) | 300 µg |
| Pantothenic Acid (as calcium pantothenate) | 20 mg |
| Calcium (as calcium carbonate, dicalcium phosphate, calcium citrate, calcium gluconate, calcium amino acid polyfructose complex) | 250 mg |
| Iron (as iron amino acid polyfructose complex) | 9 mg |
| Phosphorous (as dicalcium phosphate) | 65 mg |
| Iodine (as iodine amino acid polyfructose complex) | 150 µg |
| Magnesium (as magnesium oxide, magnesium lactate, magnesium citrate, magnesium amino acid polyfructose complex) | 200 mg |
| Zinc (zinc amino acid polyfructose complex) | 15 mg |
| Selenium (selenium amino acid polyfructose complex) | 105 µg |
| Copper (copper amino acid polyfructose complex) | 3 mg |
| Manganese (as manganese amino acid polyfructose complex) | 3 mg |
| Chromium (as chromium amino acid polyfructose complex) | 120 µg |
| Molybdenum (as molybdenum amino acid polyfructose complex) | 75 µg |
| Boron (as boron amino acid polyfructose complex) | 150 µg |

Example 8

Dietary Supplement Formulation

A dietary supplement formulation was prepared using mineral-amino acid polyfructose complexes, specifically mineral-(25:75 glycinate:aspartate) inulin complexes. The formulation was prepared by combining the components listed below in Table 5 with appropriate excipients. The combined formulation was then pressed into tablets (the daily dosage provided in Table 5 represents the amount in three tablets).

TABLE 5

|   | Total Daily Dose |
|---|---|
| Vitamin A (as beta carotene) | 3000 IU |
| Vitamin C (as ascorbic acid) | 150 mg |
| Vitamin D (as cholecalciferol) | 200 IU |
| Vitamin E (as d-alpha tocopheryl succinate) | 30 IU |
| Thiamin (as thiamin HCl) | 15 mg |
| Riboflavin | 17 mg |
| Niacin (as niacinamide) | 75 mg |
| Vitamin B6 (as pyridoxine HCl) | 10 mg |
| Folate (as folic acid) | 600 µg |
| Vitamin B12 (as cyanocobalamin) | 12 µg |
| Biotin (as d-biotin) | 60 µg |
| Pantothenic Acid (as calcium pantothenate) | 20 mg |
| Calcium (as calcium carbonate, dicalcium phosphate, calcium citrate, calcium gluconate, calcium amino acid polyfructose complex) | 250 mg |
| Phosphorous (as dicalcium phosphate) | 65 mg |

TABLE 5-continued

| | Total Daily Dose | |
|---|---|---|
| Iodine (as iodine amino acid polyfructose complex) | 150 | μg |
| Magnesium (as magnesium oxide, magnesium lactate, magnesium citrate, magnesium amino acid polyfructose complex) | 200 | mg |
| Zinc (zinc amino acid polyfructose complex) | 15 | mg |
| Selenium (as selenium amino acid polyfructose complex) | 105 | μg |
| Copper (copper amino acid polyfructose complex) | 3 | mg |
| Manganese (as manganese amino acid polyfructose complex) | 4 | mg |
| Chromium (as chromium amino acid polyfructose complex) | 120 | μg |
| Molybdenum (as molybdenum amino acid polyfructose complex) | 75 | μg |
| Boron (as boron amino acid polyfructose complex) | 150 | μg |

Example 9

Dietary Supplement Formulation

A dietary supplement formulation was prepared using mineral-amino acid polyfructose complexes, specifically mineral-(25:75 glycinate:aspartate) inulin complexes. The formulation was prepared by combining the components listed below in Table 6 with appropriate excipients. The combined formulation was then pressed into tablets (the daily dosage provided in Table 6 represents the amount in three tablets).

TABLE 6

| | Total Daily Dose | |
|---|---|---|
| Vitamin A (as beta carotene) | 3000 | IU |
| Vitamin C (as ascorbic acid) | 150 | mg |
| Vitamin D (as cholecalciferol) | 200 | IU |
| Vitamin E (as d-alpha tocopheryl succinate) | 30 | IU |
| Thiamin (as thiamin HCl) | 8.5 | mg |
| Riboflavin | 10 | mg |
| Niacin (as niacinamide) | 75 | mg |
| Vitamin B6 (as pyridoxine HCl) | 10 | mg |
| Folate (as folic acid) | 1000 | μg |
| Vitamin B12 (as cyanocobalamin) | 16 | μg |
| Biotin (as d-biotin) | 300 | μg |
| Pantothenic Acid (as calcium pantothenate) | 20 | mg |
| Calcium (as calcium carbonate, dicalcium phosphate, calcium citrate, calcium gluconate, calcium amino acid polyfructose complex) | 300 | mg |
| Iron (as iron amino acid polyfructose complex) | 9 | mg |
| Phosphorous (as dicalcium phosphate) | 65 | mg |
| Iodine (as iodine amino acid polyfructose complex) | 150 | μg |
| Magnesium (as magnesium oxide, magnesium lactate, magnesium citrate, magnesium amino acid polyfructose complex) | 225 | mg |
| Zinc (zinc amino acid polyfructose complex) | 15 | mg |
| Selenium (as selenium amino acid polyfructose complex) | 105 | μg |
| Copper (copper amino acid polyfructose complex) | 3 | mg |
| Manganese (as manganese amino acid polyfructose complex) | 2.5 | mg |
| Chromium (as chromium amino acid polyfructose complex) | 120 | μg |
| Molybdenum (as molybdenum amino acid polyfructose complex) | 75 | μg |
| Boron (as boron amino acid polyfructose complex) | 150 | μg |

Example 10

Dietary Supplement Formulation

A dietary supplement formulation was prepared using mineral-amino acid polyfructose complexes, specifically mineral-(25:75 glycinate:aspartate) inulin complexes. The formulation was prepared by combining the components listed below in Table 7 with appropriate excipients. The combined formulation was then pressed into tablets (the daily dosage provided in Table 7 represents the amount in three tablets).

TABLE 7

| | Total Daily Dose | |
|---|---|---|
| Vitamin A (as beta carotene) | 2500 | IU |
| Vitamin C (as ascorbic acid) | 80 | mg |
| Vitamin D (as cholecalciferol) | 200 | IU |
| Vitamin E (as d-alpha tocopheryl succinate) | 15 | IU |
| Thiamin (as thiamin HCl) | 0.7 | mg |
| Riboflavin | 0.8 | mg |
| Niacin (as niacinamide) | 9 | mg |
| Vitamin B6 (as pyridoxine HCl) | 1.05 | mg |
| Folate (as folic acid) | 200 | μg |
| Vitamin B12 (as cyanocobalamin) | 3 | μg |
| Biotin (as d-biotin) | 30 | μg |
| Pantothenic Acid (as calcium pantothenate) | 5 | mg |
| Calcium (as calcium carbonate, dicalcium phosphate, calcium citrate, calcium gluconate, calcium amino acid polyfructose complex) | 160 | mg |
| Iron (as iron amino acid polyfructose complex) | 5 | mg |
| Phosphorous (as dicalcium phosphate) | 20 | mg |
| Iodine (as iodine amino acid polyfructose complex) | 70 | μg |
| Magnesium (as magnesium oxide, magnesium lactate, magnesium citrate, magnesium amino acid polyfructose complex) | 40 | mg |
| Zinc (zinc amino acid polyfructose complex) | 4 | mg |
| Copper (copper amino acid polyfructose complex) | 0.5 | mg |
| Manganese (as manganese amino acid polyfructose complex) | 0.5 | mg |
| Chromium (as chromium amino acid polyfructose complex) | 10 | μg |
| Molybdenum (as molybdenum amino acid polyfructose complex) | 10 | μg |

Example 11

Dietary Supplement Formulation

A dietary supplement formulation was prepared using mineral-amino acid polyfructose complexes, specifically mineral-(25:75 glycinate:aspartate) inulin complexes. The formulation was prepared by combining the components listed below in Table 8 with appropriate excipients. The combined formulation was then pressed into tablets (the daily dosage provided in Table 8 represents the amount in three tablets).

TABLE 8

| | Total Daily Dose | |
|---|---|---|
| Vitamin A (as beta carotene) | 5000 | IU |
| Vitamin C (as ascorbic acid) | 160 | mg |
| Vitamin D (as cholecalciferol) | 400 | IU |
| Vitamin E (as d-alpha tocopheryl succinate) | 30 | IU |
| Thiamin (as thiamin HCl) | 1.4 | mg |
| Riboflavin | 1.6 | mg |
| Niacin (as niacinamide) | 18 | mg |
| Vitamin B6 (as pyridoxine HCl) | 2.1 | mg |
| Folate (as folic acid) | 400 | μg |
| Vitamin B12 (as cyanocobalamin) | 6 | μg |
| Biotin (as d-biotin) | 60 | μg |
| Pantothenic Acid (as calcium pantothenate) | 10 | mg |
| Calcium (as calcium carbonate, dicalcium phosphate, calcium citrate, calcium gluconate, calcium amino acid polyfructose complex) | 320 | mg |
| Iron (as iron amino acid polyfructose complex) | 10 | mg |
| Phosphorous (as dicalcium phosphate) | 40 | mg |
| Iodine (as iodine amino acid polyfructose complex) | 140 | μg |

TABLE 8-continued

| | Total Daily Dose |
|---|---|
| Magnesium (as magnesium oxide, magnesium lactate, magnesium citrate, magnesium amino acid polyfructose complex) | 80 mg |
| Zinc (zinc amino acid polyfructose complex) | 8 mg |
| Copper (copper amino acid polyfructose complex) | 1 mg |
| Manganese (as manganese amino acid polyfructose complex) | 1 mg |
| Chromium (as chromium amino acid polyfructose complex) | 20 µg |
| Molybdenum (as molybdenum amino acid polyfructose complex) | 20 µg |

Example 12

Dietary Supplement Formulation

A dietary supplement formulation was prepared using mineral-amino acid polyfructose complexes, specifically mineral-(25:75 glycinate:aspartate) inulin complexes. The formulation was prepared by combining the components listed below in Table 9 with appropriate excipients. The combined formulation was then pressed into tablets (the daily dosage provided in Table 9 represents the amount in three tablets).

TABLE 9

| | Total Daily Dose |
|---|---|
| Vitamin A (as beta carotene) | 3500 IU |
| Vitamin C (as ascorbic acid) | 150 mg |
| Vitamin D (as cholecalciferol) | 200 IU |
| Vitamin E (as d-alpha tocopheryl succinate) | 45 IU |
| Thiamin (as thiamin HCl) | 7.5 mg |
| Riboflavin | 8.5 mg |
| Niacin (as niacinamide) | 75 mg |
| Vitamin B6 (as pyridoxine HCl) | 10 mg |
| Folate (as folic acid) | 600 µg |
| Vitamin B12 (as cyanocobalamin) | 12 µg |
| Biotin (as d-biotin) | 60 µg |
| Pantothenic Acid (as calcium pantothenate) | 15 mg |
| Calcium (as calcium carbonate, dicalcium phosphate, calcium citrate, calcium gluconate, calcium amino acid polyfructose complex) | 250 mg |
| Phosphorous (as dicalcium phosphate) | 65 mg |
| Iodine (as iodine amino acid polyfructose complex) | 150 µg |
| Magnesium (as magnesium oxide, magnesium lactate, magnesium citrate, magnesium amino acid polyfructose complex) | 200 mg |
| Zinc (zinc amino acid polyfructose complex) | 15 mg |
| Selenium (as selenium amino acid polyfructose complex) | 105 µg |
| Copper (copper amino acid polyfructose complex) | 3 mg |
| Manganese (as manganese amino acid polyfructose complex) | 3 mg |
| Chromium (as chromium amino acid polyfructose complex) | 180 µg |
| Molybdenum (as molybdenum amino acid polyfructose complex) | 90 µg |
| Boron (as boron amino acid polyfructose complex) | 150 µg |

Example 13

Dietary Supplement Formulation

A dietary supplement formulation was prepared using mineral-amino acid polyfructose complexes, specifically mineral-(25:75 glycinate:aspartate) inulin complexes. The formulation was prepared by combining the components listed below in Table 10 with appropriate excipients. The combined formulation was then pressed into tablets (the daily dosage provided in Table 10 represents the amount in three tablets).

TABLE 10

| | Total Daily Dose |
|---|---|
| Vitamin D (as cholecalciferol) | 300 IU |
| Calcium (as calcium carbonate, dicalcium phosphate, calcium citrate, calcium gluconate, calcium amino acid polyfructose complex) | 750 mg |
| Phosphorous (as dicalcium phosphate) | 100 mg |
| Magnesium (as magnesium oxide, magnesium lactate, magnesium citrate, magnesium amino acid polyfructose complex) | 150 mg |

Example 14

Dietary Supplement Formulation

A dietary supplement formulation was prepared using mineral-amino acid polyfructose complexes, specifically mineral-(25:75 glycinate:aspartate) inulin complexes. The formulation was prepared by combining the components listed below in Table 11 with appropriate excipients. The combined formulation was then pressed into tablets (the daily dosage provided in Table 11 represents the amount in three tablets).

TABLE 11

| | Total Daily Dose |
|---|---|
| Vitamin D (as cholecalciferol) | 400 IU |
| Calcium (as calcium carbonate, dicalcium phosphate, calcium citrate, calcium gluconate, calcium amino acid polyfructose complex) | 1000 mg |
| Phosphorous (as dicalcium phosphate) | 130 mg |
| Magnesium (as magnesium oxide, magnesium lactate, magnesium citrate, magnesium amino acid polyfructose complex) | 200 mg |

Example 15

Dietary Supplement Formulation

A dietary supplement formulation was prepared using mineral-amino acid polyfructose complexes, specifically mineral-(25:75 glycinate:aspartate) inulin complexes. The formulation was prepared by combining the components listed below in Table 12 with appropriate excipients. The combined formulation was then formulated into chews (the daily dosage provided in Table 12 represents the amount in three chews).

TABLE 12

| | Total Daily Dose |
|---|---|
| Vitamin D (as cholecalciferol) | 200 IU |
| Calcium (as calcium carbonate, dicalcium phosphate, calcium citrate, calcium gluconate, calcium amino acid polyfructose complex) | 500 mg |

TABLE 12-continued

| | Total Daily Dose |
|---|---|
| Phosphorous (as dicalcium phosphate) | 64 mg |
| Magnesium (as magnesium oxide, magnesium lactate, magnesium citrate, magnesium amino acid polyfructose complex) | 100 mg |

Example 16

Dietary Supplement Formulation

A dietary supplement formulation was prepared using mineral-amino acid polyfructose complexes, specifically mineral-(25:75 glycinate:aspartate) inulin complexes. The formulation was prepared by combining the components listed below in Table 13 with appropriate excipients. The combined formulation was then pressed into tablets (the daily dosage provided in Table 13 represents the amount in three tablets).

TABLE 13

| | Total Daily Dose |
|---|---|
| Vitamin D (as cholecalciferol) | 500 IU |
| Calcium (as calcium carbonate, dicalcium phosphate, calcium citrate, calcium gluconate, calcium amino acid polyfructose complex) | 1250 mg |
| Phosphorous (as dicalcium phosphate) | 160 mg |
| Magnesium (as magnesium oxide, magnesium lactate, magnesium citrate, magnesium amino acid polyfructose complex) | 250 mg |

Example 17

Preparation of Magnesium-Amino Acid Inulin Complex 126.8 grams of magnesium oxide was mixed with 670.1 grams of aspartic acid, 94.5 grams of glycine, and 108.6 grams of inulin (degree of polymerization 8-13). 78 mL of water was added. The mixture was heated to 120° F. with stirring for 20 minutes. The mixture was then transferred into drying trays, and was dried overnight or until the composition reached a moisture content of 8%.

Example 18

The Oxidation Rate of Multivitamin/Multimineral Compositions

The oxidation rate of two commercially available multivitamin/multimineral compositions were compared: one uses typical mineral forms (Formula A), and the other uses mineral-amino acid polysaccharide complexes (Formula B).

TABLE 14

| | Formula A | | Formula B | |
|---|---|---|---|---|
| Vitamin A | 3500 IU | | 3000 IU | |
| Vitamin C | 90 mg | | 150 mg | |
| Vitamin D | 400 IU | | 200 IU | |
| Vitamin E | 45 IU | | 30 IU | |
| Vitamin K | 20 mcg | | | |
| Thiamin | 1.2 mg | | 15 mg | |
| Riboflavin | 1.7 mg | | 17 mg | |
| Niacin | 16 mg | | 75 mg | |
| Vitamin B6 | 3 mg | | 10 mg | |
| Folate | 400 mcg | | 600 mcg | |
| Vitamin B12 | 18 mcg | | 12 mcg | |
| Biotin | 30 mcg | | 60 mcg | |
| Pantothenic Acid | 5 mcg | | 20 mg | |
| Calcium | 210 mg | | 250 mg | |
| Iodine | | | 150 mcg | |
| Magnesium | 120 mg | | 200 mg | |
| Zinc | 15 mg | as zinc oxide | 15 mg | as zinc AAOS complex |
| Selenium | 105 mcg | as sodium selenate | 105 mcg | as selenium AAOS complex |
| Copper | 2 mg | as cupric oxide | 3 mg | as copper AAOS complex |
| Manganese | 2 mg | as manganese sulfate | 4 mg | as manganese AAOS complex |
| Chromium | 120 mcg | as chromium chloride | 120 mcg | as chromium AAOS complex |
| Molybdenum | | | 75 mcg | |
| Boron | | | 150 mcg | |
| Lycopene | 600 mcg | | | |

Oxidation of ascorbic acid catalyzed by copper was evaluated by monitoring oxygen consumption. Tablets were crushed to a thin powder. An aliquot of both samples, which provided an equal amount of copper, was used. Samples were incubated in 0.1N HCl for 1 hour, and then the pH was adjusted to 7.0 with sodium carbonate. Ascorbic acid was added to provide at an equal concentration in both samples. The final concentration of copper was 3.9 µM and ascorbate was 600 µM. 3 mL of each mixture was placed in a measuring cell equipped with a Clark electrode. The oxygen concentration was monitored with a BioStat Nitric Oxide System (ESA Biosciences, Chelmsford, Mass.). The oxygen consumption rate for Formula A was 319 pmol/sec, while Formula B had a consumption rate of 75 pmol/sec.

Example 19

EPR Spectroscopy of Copper Complexes

EPR spectroscopy was used to probe the nature of the aqueous copper complexes at different pH values. All EPR measurements were done in using a Bruker ER-200 X-band EPR spectrometer. Samples (50 µL) in capillary tubes (0.5 mm i.d.) were examined at room temperature. Instrumental conditions included: microwave frequency 9.71 GHz; center field 3415 G; scan rate 1000 G/100 s; modulation amplitude 2.5 G; time constant 0.5 s; microwave power $10^2$ mW; instrument gain varied for different samples from $10^3$ to $3.2 \times 10^5$. Manganese in calcium oxide was used as a reference for EPR parameters.

Figure 4:
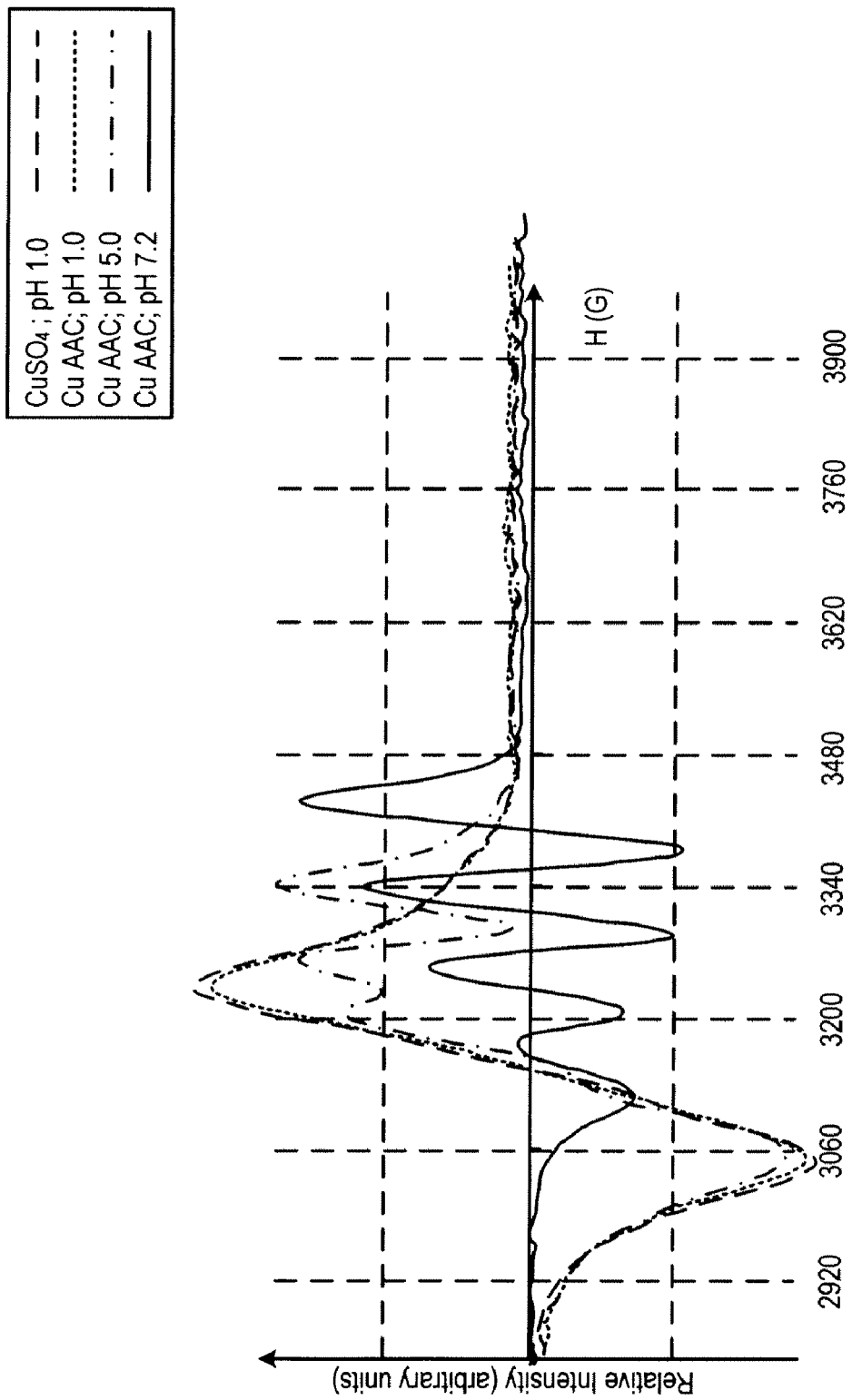
FIG. 4 is a line graph of the EPR spectra of copper(II) compounds in different pH environments.

When either $CuSO_4$ or copper-amino acid (glycinate or aspartate) inulin complex (CuAAC; 5 mM) was dissolved in aqueous solution at pH 1 the EPR spectra was a single line (g=2.19; $\Delta H_{pp}$=140 G), FIG. 4. Similar spectra were observed when these complexes were dissolved in 0.5 M perchloric acid consistent with the aquo-complex of copper. However, at near-neutral pH, the EPR of the ACC complex changed to that expected for a histidine-type complex (see Basosi R, Pogni R, Lunga G D. Coordination modes of histidine moiety in copper (II) dipeptide complexes detected by multifrequency ESR. Bull Magn Res 1992; 14:224-8). This indicates that at neutral pH, typical amino acids can become ligands to copper(II).

Example 20

Ascorbyl Radical Kinetics

Figure 5A:
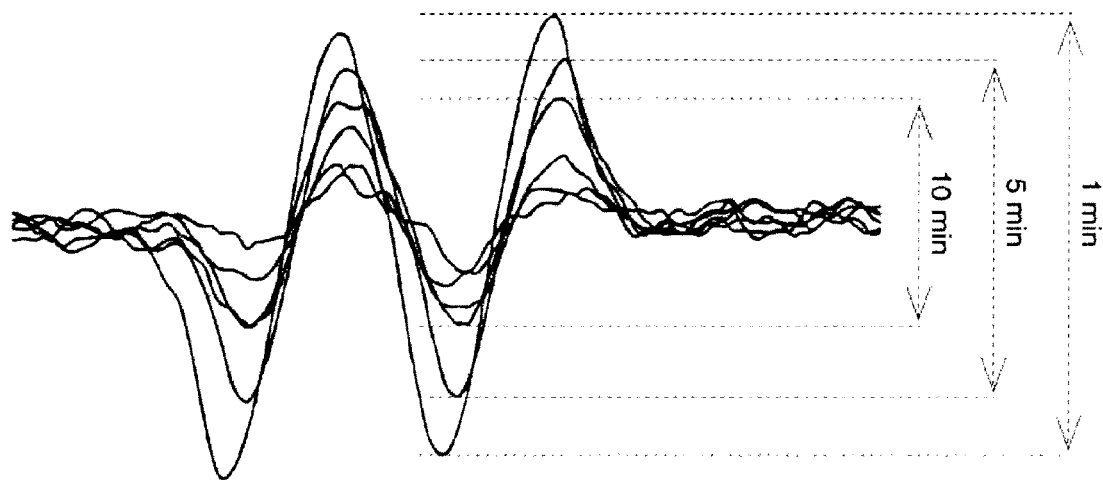
FIG. 5A is a line graph showing the loss of ascorbate absorbance as a function of time following addition of copper.
Figure 5B:
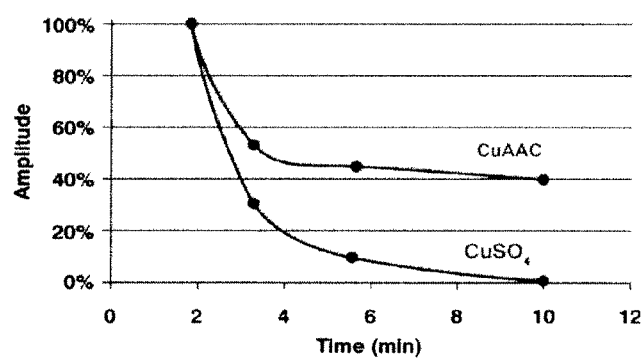
FIG. 5B is a line graph indicating that amino-acid polysaccharide complexing slows copper-catalyzed oxidation of ascorbate, compared to its sulfate form.

Ascobyl radical kinetics were measured as described in Example 4 to determine whether the rate of copper-catalyzed ascorbate oxidation was affected by the addition of either CuSO4 or a copper-amino acid (glycinate or aspartate) inulin complex (CuAAC). As shown in FIG. 5, the introduction of copper to near-neutral solutions of ascorbate resulted in an increase in the concentration of the ascorbate radical. However, the rate of loss of this radical was significantly slowed by the CuAAC compared to the sulfate form of this metal. The loss of ascorbate radical in this system will parallel the loss of ascorbate. Thus, these results indicate that the AAC complex slows the catalytic oxidcation of ascorbate by copper.

Example 21

Copper-Mediated Oxidation of Trolox is Inhibited by CuAAC

Trolox is an analogue of vitamin E, a lipid soluble antioxidant; the phytyl tail of α-tocopherol has been replaced by a carboxyl group making Trolox water-soluble. It is a tool used to probe for antioxidant-capacity and free radical flux. The one-electron oxidation of Trolox results in the formation of a phenoxyl radical that is readily detected by EPR. All EPR measurements were done in using a Bruker ER-200 X-band EPR spectrometer. Samples (50 µL) in capillary tubes (0.5 mm i.d.) were examined at room temperature. Instrumental conditions included: microwave frequency 9.71 GHz; center field 3472 G; scan range 60 G; scan time 50 s; mod amp 1.0 G; time constant 0.5 s; microwave power 20 mW; and instrument gain $2 \times 10^6$.

Figure 6A:
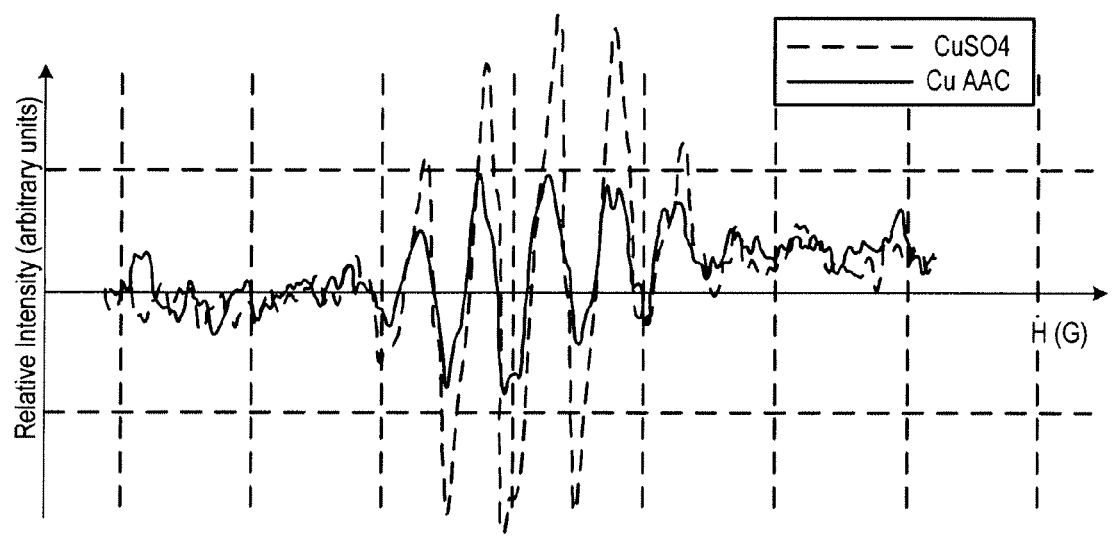
FIG. 6A is a line graph of the EPR spectrum of the Trolox phenoxyl radical formed upon addition of copper to a system.
Figure 6B:
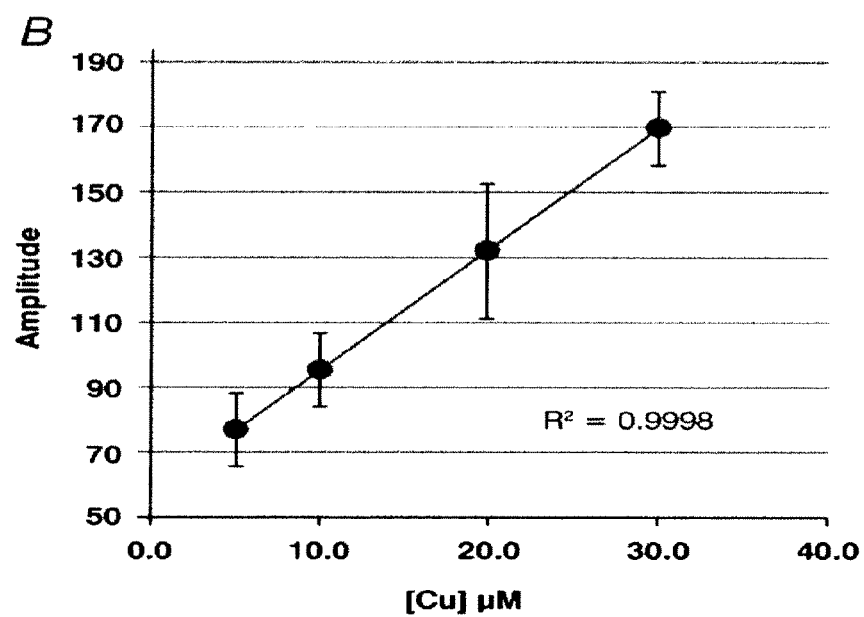
FIG. 6B is a line graph of the linear dose-response curve for addition of varying amounts of $CuSO_4$ to this system.

Using a Fenton system to initiate oxidations, the formation of the Trolox free radical was observed upon the introduction of copper (FIG. 6A). The concentration of the Trolox free radical was directly proportional to the amount of $Cu^{2+}$ introduced into the system (FIG. 6B). Thus, this system appears to be excellent for determining the effectiveness of metals in initiating oxidation processes that will consume antioxidants.

When copper with different coordination environments or matrices was introduced into this system, the intensity of the EPR spectrum of Trolox radical varied with the environment. Copper sulfate produced a robust EPR signal of the Trolox free radical; when gluconate was available to coordinate the copper, the EPR signal was reduced by about 15%; however, when copper was introduced as part of an AAC complex, the EPR signal intensity was reduced by approximately 50%, compared to $CuSO_4$. This is consistent with the observations with ascorbate indicating that mineral-AAC reduces the oxidative flux in a system.

Example 22

Preparation of Mineral

Amino Acid Polysaccharide Complexes

A copper-amino acid polysaccharide complex was prepared by suspending Cu carbonate with glycine or aspartic acid followed by inulin at final ratio 1:4:01. After stirring for 10 min at 80° C., the mixture was dried in oven.

An iron-amino acid complex was prepared by first dissolving $FeSO_4$ (1 mol) in water; then NaOH was added to precipitate the iron. Glycine or aspartic acid (2 moles) was added to a suspension of the Fe-solids, and the mixture was stirred and then dried in an oven. To prepare the iron-amino acid polysaccharide complex, glycine or aspartic acid (1 mole) was suspended in water with the iron solids; then 0.01 mole of inulin was added. After heating at 80° C., the resulting mixture was dried in oven.

Example 23

Mineral Solubility

Two forms of zinc, copper, and iron were tested for solubility at conditions close to physiological. Mineral-amino acid polysaccharide complexes were compared with inorganic forms: zinc oxide, copper sulfate, and iron sulfate. Samples, in an amount equivalent to 20 tablets, were suspended in 20 mL of water. The pH was adjusted to 1-1.2 and maintained for one hour, simulating a gastric environment. After the first hour, the pH was adjusted to 7-7.2 and maintained for another hour, simulating an intestinal environment. The product was then centrifuged and the supernatant taken for analysis. Results are presented as a percent of solubilized mineral, and the elemental recovery data is shown in Table 15.

TABLE 15

|  | Inorganic Form (Sulfates and Oxide) | Mineral - amino acid polysaccharide complexes |
|---|---|---|
| Zinc | 1.2% | 97.0% |
| Copper | 15.6% | 100.0% |
| Iron | 19.6% | 92.5% |

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A complex of one or more mineral-amino acid compounds conjugated to one or more polysaccharides, wherein said complex is prepared by a process comprising heating a composition consisting of water, one or more mineral-amino acid compounds, and one or more polysaccharides at a temperature from about 100° F. to about 180° F. to form said complex.

2. The complex of claim 1, wherein the process further comprises drying said complex.

3. The complex of claim 1, wherein said composition is heated for from about 5 minutes to about 30 minutes.

4. The complex of claim 3, wherein said composition is heated for about 20 minutes.

5. The complex of claim 1, wherein said composition is heated at about 160° F.

6. A process of preparing a complex of one or more mineral-amino acid compounds conjugated to one or more polysaccharides, the process comprising heating a composition consisting of water, one or more mineral-amino acid compounds and one or more polysaccharides at a temperature from about 100° F. to about 180° F. to form said complex.

7. A composition comprising a complex of one or more mineral-amino acid compounds conjugated to one or more polysaccharides.

8. The composition of claim 7, wherein said composition comprises two or more complexes selected from the group consisting of: a calcium amino acid polyfructose complex; iron amino acid polyfructose complex; iodine amino acid polyfructose complex; magnesium amino acid polyfructose complex; zinc amino acid polyfructose complex; selenium amino acid polyfructose complex; copper amino acid polyfructose complex; manganese amino acid polyfructose complex; molybdenum amino acid polyfructose complex; and boron amino acid polyfructose complex.

9. The composition of claim 7, further comprising one or more of vitamin A; vitamin C; vitamin D; vitamin E; vitamin K; thiamin; riboflavin; niacin; vitamin B6; folate; vitamin B12; biotin; pantothenic acid; and phosphorous.

10. The composition of claim 7, wherein said composition is in the form of a daily dosage, and wherein said composition comprises:
(a) 1-5000 IU vitamin A;
(b) 30-240 mg vitamin C;
(c) 1-600 IU vitamin D;
(d) 15-60 IU vitamin E;
(e) 0-56 μg vitamin K;
(f) 1.5-15 mg thiamin;
(g) 1.7-17 mg riboflavin;
(h) 20-100 mg niacin;
(i) 2-20 mg vitamin B6;
(j) 200-800 μg folate;
(k) 6-18 μg vitamin B12;
(l) 20-400 μg biotin;
(m) 10-200 mg pantothenic acid;
(n) 200-1000 mg calcium salt or complex;
(o) 0-18 mg iron amino acid polyfructose complex;
(p) 0-300 mg phosphorous;
(q) 100-300 μg iodine amino acid polyfructose complex;
(r) 100-400 mg magnesium salt or complex;
(s) 5-30 mg zinc amino acid polyfructose complex;
(t) 35-150 μg selenium amino acid polyfructose complex;
(u) 1-5 mg copper amino acid polyfructose complex;
(v) 1-5 mg manganese amino acid polyfructose complex;
(w) 60-360 μg chromium amino acid polyfructose complex;
(x) 50-150 μg molybdenum amino acid polyfructose complex; and
(y) 0-300 μg boron amino acid polyfructose complex.

11. The composition of claim 10, wherein one or more of said calcium salt or complex and said magnesium salt or complex is a corresponding mineral-amino acid polyfructose complex.

12. The composition of claim 7, wherein said composition is in the form of a daily dosage, and wherein ef said composition comprises:
(a) 3000 IU vitamin A;
(b) 150 mg vitamin C;
(c) 200 IU vitamin D;
(d) 30 IU vitamin E;
(e) 28 μg vitamin K;
(f) 15 mg thiamin;
(g) 17 mg riboflavin;
(h) 75 mg niacin;
(i) 10 mg vitamin B6;
(j) 800 μg folate;
(k) 12 μg vitamin B12;
(l) 300 μg biotin;
(m) 20 mg pantothenic acid;
(n) 250 mg calcium salt or complex;
(o) 9 mg iron amino acid polyfructose complex;
(p) 65 mg phosphorous;
(q) 150 μg iodine amino acid polyfructose complex;
(r) 200 mg magnesium salt or complex;
(s) 15 mg zinc amino acid polyfructose complex;
(t) 105 μg selenium amino acid polyfructose complex;
(u) 3 mg copper amino acid polyfructose complex;
(v) 2.5 mg manganese amino acid polyfructose complex;
(w) 120 μg chromium amino acid polyfructose complex;
(x) 75 μg molybdenum amino acid polyfructose complex; and
(y) 150 μg boron amino acid polyfructose complex.

13. The composition of claim 7, wherein said composition is in the form of a daily dosage, and wherein said composition comprises:
(a) 3000 IU vitamin A;
(b) 150 mg vitamin C;
(c) 200 IU vitamin D;
(d) 30 IU vitamin E;
(e) 15 mg thiamin;
(f) 17 mg riboflavin;
(g) 75 mg niacin;
(h) 10 mg vitamin B6;
(i) 600 μg folate;
(j) 12 μg vitamin B12;
(k) 60 μg biotin;
(l) 20 mg pantothenic acid;
(m) 250 mg calcium salt or complex;
(n) 65 mg phosphorous;
(o) 150 μg iodine amino acid polyfructose complex;
(p) 200 mg magnesium salt or complex;
(q) 15 mg zinc amino acid polyfructose complex;
(r) 105 μg selenium amino acid polyfructose complex;
(s) 3 mg copper amino acid polyfructose complex;
(t) 4 mg manganese amino acid polyfructose complex;
(u) 120 μg chromium amino acid polyfructose complex;
(v) 75 μg molybdenum amino acid polyfructose complex; and
(w) 150 μg boron amino acid polyfructose complex.

14. The composition of claim 7, wherein said composition is in the form of a daily dosage, and wherein said composition comprises:
(a) 3000 IU vitamin A;
(b) 150 mg vitamin C;
(c) 200 IU vitamin D;
(d) 30 IU vitamin E;
(e) 8.5 mg thiamin;
(f) 10 mg riboflavin;
(g) 75 mg niacin;
(h) 10 mg vitamin B6;
(i) 1000 µg folate;
(j) 16 µg vitamin B12;
(k) 300 µg biotin;
(l) 20 mg pantothenic acid;
(m) 300 mg calcium salt or complex;
(n) 9 mg iron amino acid polyfructose complex;
(o) 65 mg phosphorous;
(p) 150 µg iodine amino acid polyfructose complex;
(q) 225 mg magnesium salt or complex;
(r) 15 mg zinc amino acid polyfructose complex;
(s) 105 µg selenium amino acid polyfructose complex;
(t) 3 mg copper amino acid polyfructose complex;
(u) 2.5 mg manganese amino acid polyfructose complex;
(v) 120 µg chromium amino acid polyfructose complex;
(w) 75 µg molybdenum amino acid polyfructose complex; and
(x) 150 µg boron amino acid polyfructose complex.

15. The composition of claim 7, wherein said composition is in the form of a daily dosage, and wherein said composition comprises:
(a) 2500 IU vitamin A;
(b) 80 mg vitamin C;
(c) 200 IU vitamin D;
(d) 15 IU vitamin E;
(e) 0.7 mg thiamin;
(f) 0.8 mg riboflavin;
(g) 9 mg niacin;
(h) 1.05 mg vitamin B6;
(i) 200 µg folate;
(j) 3 µg vitamin B12;
(k) 30 µg biotin;
(l) 5 mg pantothenic acid;
(m) 160 mg calcium salt or complex;
(n) 5 mg iron amino acid polyfructose complex;
(o) 20 mg phosphorous;
(p) 70 µg iodine amino acid polyfructose complex;
(q) 40 mg magnesium salt or complex;
(r) 4 mg zinc amino acid polyfructose complex;
(s) 0.5 mg copper amino acid polyfructose complex;
(t) 0.5 mg manganese amino acid polyfructose complex;
(u) 10 µg chromium amino acid polyfructose complex; and
(v) 10 µg molybdenum amino acid polyfructose complex.

16. The composition of claim 7, wherein said composition is in the form of a daily dosage, and wherein said composition comprises
(a) 5000 IU vitamin A;
(b) 160 mg vitamin C;
(c) 400 IU vitamin D;
(d) 30 IU vitamin E;
(e) 1.4 mg thiamin;
(f) 1.6 mg riboflavin;
(g) 18 mg niacin;
(h) 2.1 mg vitamin B6;
(i) 400 µg folate;
(j) 6 µg vitamin B12;
(k) 60 µg biotin;
(l) 10 mg pantothenic acid;
(m) 320 mg calcium salt or complex;
(n) 10 mg iron amino acid polyfructose complex;
(o) 40 mg phosphorous;
(p) 140 µg iodine amino acid polyfructose complex;
(q) 80 mg magnesium salt or complex;
(r) 8 mg zinc amino acid polyfructose complex;
(s) 1 mg copper amino acid polyfructose complex;
(t) 1 mg manganese amino acid polyfructose complex;
(u) 20 µg chromium amino acid polyfructose complex; and
(v) 20 µg molybdenum amino acid polyfructose complex.

17. The composition of claim 7, wherein said composition is in the form of a daily dosage, and wherein said composition comprises:
(a) 3500 IU vitamin A;
(b) 150 mg vitamin C;
(c) 200 IU vitamin D;
(d) 45 IU vitamin E;
(e) 7.5 mg thiamin;
(f) 8.5 mg riboflavin;
(g) 75 mg niacin;
(h) 10 mg vitamin B6;
(i) 600 µg folate;
(j) 12 µg vitamin B12;
(k) 60 µg biotin;
(l) 15 mg pantothenic acid;
(m) 250 mg calcium salt or complex;
(n) 65 mg phosphorous;
(o) 150 µg iodine amino acid polyfructose complex;
(p) 200 mg magnesium salt or complex;
(q) 15 mg zinc amino acid polyfructose complex;
(r) 105 µg selenium amino acid polyfructose complex;
(s) 3 mg copper amino acid polyfructose complex;
(t) 3 mg manganese amino acid polyfructose complex;
(u) 180 µg chromium amino acid polyfructose complex;
(v) 90 µg molybdenum amino acid polyfructose complex; and
(w) 150 µg boron amino acid polyfructose complex.

18. The composition of claim 7, wherein said composition is in the form of a daily dosage, and wherein ef said composition comprises:
(a) 300 IU vitamin D;
(b) 750 mg calcium salt or complex;
(c) 100 mg phosphorous; and
(d) 150 mg magnesium salt or complex.

19. The composition of claim 7, wherein said composition is in the form of a daily dosage, and wherein said composition comprises:
(a) 400 IU vitamin D;
(b) 1000 mg calcium salt or complex;
(c) 130 mg phosphorous; and
(d) 200 mg magnesium salt or complex.

20. The composition of claim 7, wherein said composition is in the form of a daily dosage, and wherein said composition comprises:
(a) 500 IU vitamin D;
(b) 1250 mg calcium salt or complex;
(c) 160 mg phosphorous; and
(d) 250 mg magnesium salt or complex.

21. The composition of claim 12, wherein one or more of said calcium salt or complex and said magnesium salt or complex comprises a corresponding mineral-amino acid polyfructose complex.

22. A complex of a mineral-amino acid compound conjugated to a polysaccharide, wherein said complex diffuses across a 3500 MW cutoff dialysis membrane slower than an uncomplexed mixture of said mineral-amino acid compound and said polysaccharide.

23. The complex of claim 22, wherein said mineral is selected from the group consisting of Ca, Mg, K, Zn, Cu, Fe, I, Mn, Mo, Se, and Cr.

24. The complex of claim 22, wherein said amino acid is a natural amino acid.

25. The complex of claim 23, wherein said amino acid is selected from the group consisting of L-alanine, L-arginine, L-asparagine, L-aspartic acid, L-cysteine, L-glutamic acid, L-glutamine, L-glycine, L-histidine, L-isoleucine, L-leucine, L-lysine, L-methionine, L-phenylalanine, L-proline, L-serine, L-threonine, L-tryptophan, L-tyrosine, L-valine, and mixtures thereof.

26. The complex of claim 22, wherein said amino acid is selected from the group consisting of L-glycine and L-aspartic acid.

27. The complex of claim 22, wherein said polysaccharide is selected from the group consisting of cellulose; polyhexoses; polypentoses; polydextrose; starch; polygalactan; polymannan; chitin; chitosan; chondroitin; polyfructose; inulin; and pectin.

28. The complex of claim 22, wherein said polysaccharide is a cellulose.

29. The complex of claim 22, wherein said polysaccharide is a polyfructose.

30. The complex of claim 22, wherein said polysaccharide is inulin.

31. The complex of claim 22, wherein said polysaccharide is polydextrose.

32. The complex of claim 1, wherein administration of said complex to a mammal results in a reduced rate of free radical formation in said mammal compared to administration of said mineral as an inorganic salt.

33. The complex of claim 32, wherein said free radical is a reactive oxygen species.

34. The composition of claim 7, wherein said composition comprises two different complexes of one or more mineral-amino acid compounds conjugated to one or more polysaccharides.

35. The composition of claim 7, wherein administration of said composition to a mammal results in a reduced rate of free radical formation in said mammal compared to administration of a composition comprising said two or more minerals as inorganic salts.

36. The complex of claim 22, wherein administration of said complex to a mammal results in a reduced rate of free radical formation in said mammal compared to administration of said mineral as an inorganic salt.

* * * * *

UNITED STATES PATENT AND TRADEMARK OFFICE
CERTIFICATE OF CORRECTION

PATENT NO. : 8,273,393 B2  
APPLICATION NO. : 12/499929  
DATED : September 25, 2012  
INVENTOR(S) : Alexander B. Rabovsky et al.

Page 1 of 1

It is certified that error appears in the above-identified patent and that said Letters Patent is hereby corrected as shown below:

Title Page, item [56], Column 2, line 41, please delete "inestinal" and insert --intestinal--, therefor.

Column 28, line 9 (Claim 12), after "wherein" please delete "ef".

Column 29, line 56 (Claim 16), please delete "comprises" and insert --comprises:--, therefor.

Column 30, line 42 (Claim 18), after "wherein" please delete "ef".

Signed and Sealed this
Nineteenth Day of February, 2013

Teresa Stanek Rea
*Acting Director of the United States Patent and Trademark Office*